United States Patent
Vladimirova et al.

(10) Patent No.: US 11,462,325 B2
(45) Date of Patent: Oct. 4, 2022

(54) MULTIMODAL MACHINE LEARNING BASED CLINICAL PREDICTOR

(71) Applicant: Roche Molecular Systems, Inc., Pleasanton, CA (US)

(72) Inventors: Antoaneta Petkova Vladimirova, Mountain View, CA (US); Yogesh P. Pandit, Fremont, CA (US); Vishakha Sharma, Foster City, CA (US); Tod M. Klingler, San Carlos, CA (US); Hari Singhal, Foster City, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 261 days.

(21) Appl. No.: 16/588,289

(22) Filed: Sep. 30, 2019

(65) Prior Publication Data
US 2020/0105413 A1   Apr. 2, 2020

Related U.S. Application Data

(60) Provisional application No. 62/739,189, filed on Sep. 29, 2018.

(51) Int. Cl.
  *G16H 50/20*   (2018.01)
  *G16H 20/30*   (2018.01)
  (Continued)

(52) U.S. Cl.
  CPC .......... *G16H 50/20* (2018.01); *G06T 7/0012* (2013.01); *G06V 20/69* (2022.01); *G16B 20/00* (2019.02);
  (Continued)

(58) Field of Classification Search
  CPC ........ G16H 50/20; G16H 10/40; G16H 15/00; G16H 20/30; G16H 50/30; G06K 9/00127;
  (Continued)

(56) References Cited

U.S. PATENT DOCUMENTS

2009/0105167 A1 *  4/2009  Potti ..................... G16B 40/20
                                                          514/34
2009/0156906 A1    6/2009  Liebman
(Continued)

OTHER PUBLICATIONS

Khosravi et al., Deep Convolutional Neural Networks Enable Discrimination of Heterogeneous Digital Pathology Images, 27 eBiomedicine 317-328 (Jan. 2018) (Year: 2018).*
(Continued)

*Primary Examiner* — Evangeline Barr
*Assistant Examiner* — Jordan L Jackson
(74) *Attorney, Agent, or Firm* — Kilpatrick Townsend and Stockton LLP

(57) ABSTRACT

Methods and systems for performing a clinical prediction are provided. In one example, the method comprises: receiving first molecular data of a patient, the first molecular data including at least gene expressions of the patient; receiving first biopsy image data of the patient; processing, using a machine learning model, the first molecular data and the first biopsy image data to perform a clinical prediction of the patient's response to a treatment, wherein the machine learning model is generated or updated based on second molecular data including at least gene expressions and second biopsy image data of a plurality of patients; and generating an output of the clinical prediction.

19 Claims, 16 Drawing Sheets

(51) Int. Cl.
*G16H 10/40* (2018.01)
*G16H 15/00* (2018.01)
*G16H 50/30* (2018.01)
*G16B 40/00* (2019.01)
*G16B 20/00* (2019.01)
*G06T 7/00* (2017.01)
*G06V 20/69* (2022.01)

(52) U.S. Cl.
CPC ............ *G16B 40/00* (2019.02); *G16H 10/40* (2018.01); *G16H 15/00* (2018.01); *G16H 20/30* (2018.01); *G16H 50/30* (2018.01)

(58) Field of Classification Search
CPC ...... G06T 7/0012; G16B 20/00; G16B 40/00; G06Q 50/20–26
See application file for complete search history.

(56) References Cited

U.S. PATENT DOCUMENTS

| | | | | |
|---|---|---|---|---|
| 2015/0267259 A1* | 9/2015 | Kuznetsov | ............ | C12N 15/111 514/19.3 |
| 2017/0270666 A1* | 9/2017 | Barnes | ...................... | G06T 7/12 |
| 2018/0068083 A1 | 3/2018 | Cohen et al. | | |
| 2018/0226153 A1* | 8/2018 | Rubenstein | ............ | G16H 50/50 |
| 2018/0275145 A1* | 9/2018 | Axtell | .................... | G16B 20/20 |

OTHER PUBLICATIONS

Lieber et al., Prognosis of ovarian cancer is associated with effector memory CD8+ T cell accumulation in ascites, CXCL9 levels and activation-triggered signal transduction in T cells, 7(5) Oncoimmunology (Mar. 2018) (Year: 2018).*

Keren et al., A Structured Tumor-Immune Microenvironment in Triple Negative Breast Cancer Revealed by Multiplexed Ion Beam Imaging, 174(6) Cell 1373-1387 (Sep. 6, 2018) (Year: 2018).*

Sun et al., A radiomics approach to assess tumour-infiltrating CD8 cells and response to anti-PD-1 or anti-PD-L1 immunotherapy: an imaging biomarker, retrospective multicohort study, 19(9) The Lancet Oncology 1180-1191 (Aug. 14, 2018) (Year: 2018).*

Ohgami et al., Large B-cell lymphomas poor in B cells and rich in PD-1+ T cells can mimic T-cell lymphomas, 142(2) Am J Clin Pathology 150-156 (Aug. 2014) (Year: 2014).*

International Search Report and Written Opinion in PCT/US2019/053809 dated Jan. 3, 2020; 14 pages.

* cited by examiner

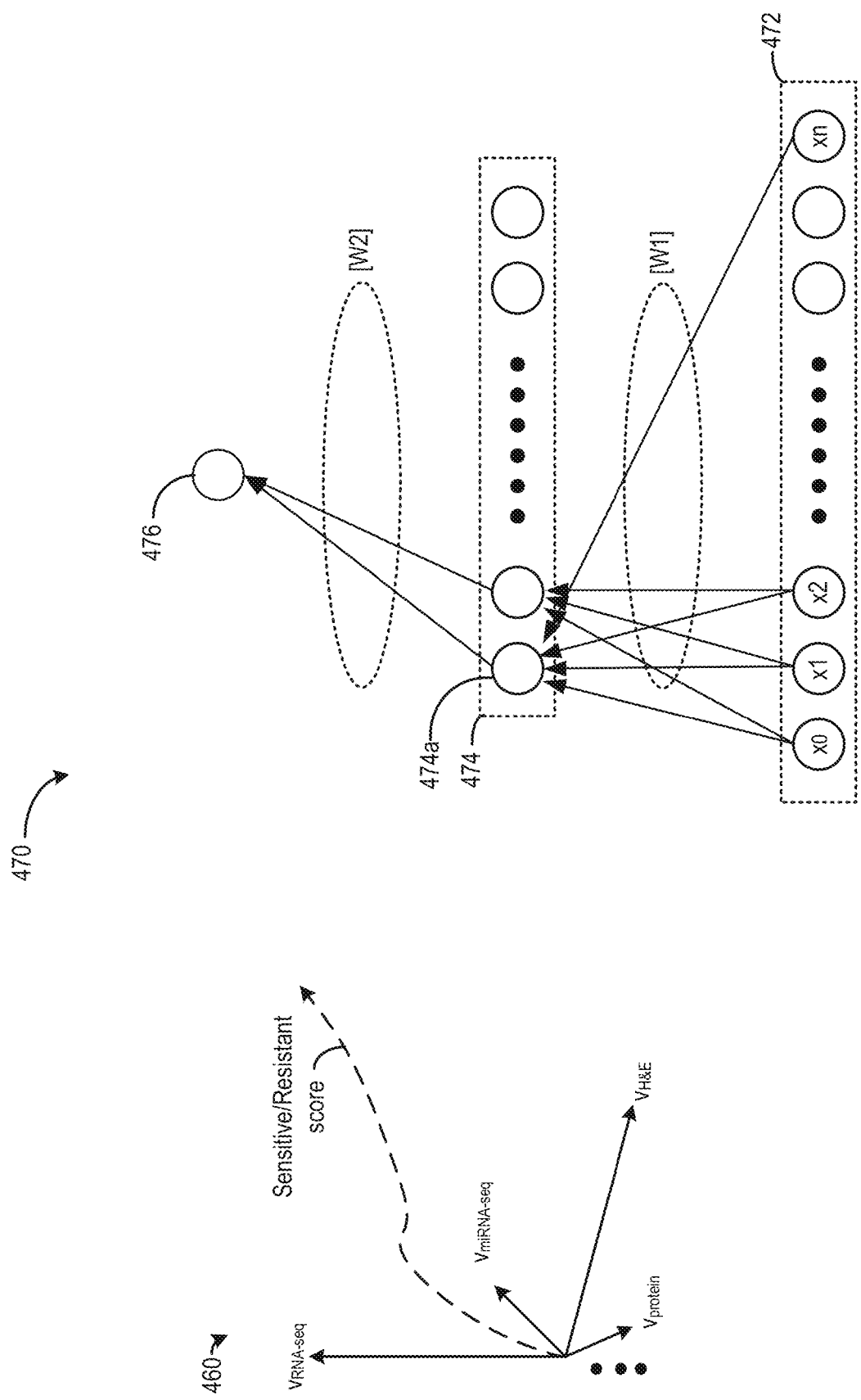

MULTIMODAL MACHINE LEARNING BASED CLINICAL PREDICTOR

CROSS-REFERENCES TO RELATED APPLICATIONS

The present application claims benefit of priority to U.S. Provisional Patent Application No. 62/739,189, filed Sep. 29, 2018, the content of which is herein incorporated by reference in its entirety for all purposes.

BACKGROUND

Cancer is a frightening disease, as early detection can be difficult for many cancer types, and those cancers may have progressed to advanced stages when they are diagnosed. For example, ovarian cancer accounts for about 3% of deaths among women and has been termed the "silent killer" because the presenting symptoms are often mistaken for other benign conditions. Likewise, the early signs of lung cancer, such as cough and chest pain, can also be mistaken for other more benign diseases (e.g., cold). Additionally, many cancer patients who follow the standard of care, which includes, for example, surgery followed by platinum-based chemotherapy, may develop resistance to the platinum treatment. Thus, the ability to predict which patient may become resistant and relapse may prompt consideration of additional therapeutic options, such as available clinical trials, earlier in the patient journey, which can increase the odds of recovery and survival. However, currently there lacks a predictor that can accurately predicts a patient's response to a cancer treatment.

BRIEF SUMMARY

Disclosed herein are techniques for performing a clinical prediction based on multimodal clinical data using a machine learning model. Multimodal clinical data generally refer to clinical data of different types of clinical data, such as molecular data, biopsy image data, etc. As examples, the clinical prediction may include predicting a response to a treatment for a disease, predicting a risk of the patient having the disease, outcome prediction, biomarker derivation, or target identification for drug development, etc. One example of the clinical prediction includes predicting whether the patient may be resistant or sensitive to a platinum drug treatment for ovarian cancer. Another example of the clinical prediction includes predicting the survival rate of the patient for different types of treatments (e.g., immunotherapy, chemotherapy, etc.) for lung cancer. The techniques can also be applied to other diseases areas and for other clinical hypotheses.

In some embodiments, the techniques include receiving multimodal clinical data of a patient, which can include first molecular data and first biopsy image data. The techniques further include processing, using a machine learning model, the first molecular data and the first biopsy image data to perform a clinical prediction. The machine learning model is generated or updated based on second molecular data and second biopsy image data of a plurality of patients. The techniques further include generating an output of the clinical prediction.

The molecular data may include numerical feature vectors representing, for example, one or more RNA-seq (ribonucleic acid (RNA)-sequencing) data, one or more microRNA-seq (miRNA sequencing) data, protein expression data, gene mutation data, deoxyribonucleic acid (DNA) methylation data, or copy number variation (CNV) data, presence of certain protein molecules (e.g., antibody, such as PD-L1) in a patient, etc. RNA-seq data and miRNA-seq data can include gene expression patterns included in the RNAs and miRNAs. The biopsy image data may comprise biopsy image data of primary tumor, such as hematoxylin- and eosin-stained (H&E) histopathology data. The machine learning model may include, for example, a Naive Bayes (NB) model, a logistic regression (LR) model, a random forest (RF) model, a support vector machine (SVM) model, an artificial neural network model, a multilayer perceptron (MLP) model, a convolutional neural network (CNN), other machine learning or deep leaning models, etc. The machine learning model can be updated/trained using a supervised learning technique, an unsupervised learning technique, etc.

These and other embodiments of the invention are described in detail below. For example, other embodiments are directed to systems, devices, and computer readable media associated with methods described herein.

A better understanding of the nature and advantages of embodiments of the present invention may be gained with reference to the following detailed description and the accompanying drawings.

BRIEF DESCRIPTION OF THE DRAWINGS

The detailed description is set forth with reference to the accompanying figures.

FIG. 4A, FIG. 4B, FIG. 4C, FIG. 4D, FIG. 4E, and FIG. 4F provide illustrate examples of features extracted from multimodal clinical data and examples of clinical prediction models, according to certain aspects of this disclosure.

DETAILED DESCRIPTION

Figure 1A:
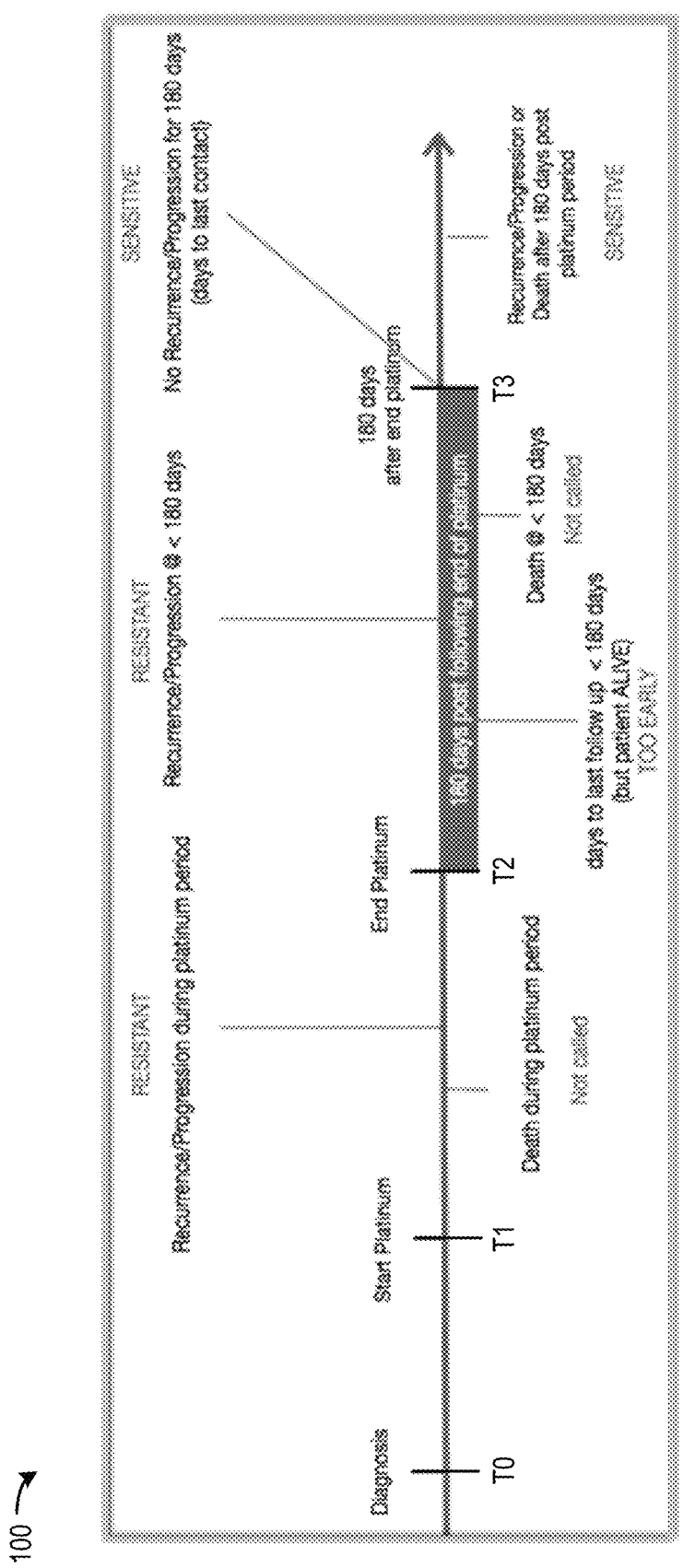
FIG. 1A and FIG. 1B illustrate example techniques for analyzing treatment responses of patients, according to certain aspects of this disclosure.

Disclosed herein are techniques for performing a clinical prediction. The clinical prediction may include predicting a response to a treatment for a disease, predicting a risk of the patient having the disease, etc. One example of the clinical prediction includes predicting whether the patient is resistant or sensitive to a platinum drug treatment for ovarian cancer. Disclosed techniques can be used for treatment for other cancer types, to answer other clinical questions, etc.

More specifically, multimodal clinical data, such as molecular data and biopsy image data of a patient having a disease to be treated can be collected, and processed using a machine learning model to perform a clinical prediction of the patient's response to a treatment. The molecular data may include, for example, RNA-seq, miRNA-seq, protein expression data, gene mutation data, deoxyribonucleic acid (DNA) methylation data, copy number variation (CNV) data, etc. Numerical feature vectors can be generated to represent the molecular data based on, for example, a mapping between the molecular data (e.g., gene expressions) and pre-determined codes.

The biopsy image data may include numerical feature vectors extracted from a biopsy image such as, for example, a biopsy image of primary tumor. The biopsy image can be pre-processed to include hematoxylin- and eosin-stained (H&E) histopathology data. The numerical feature vectors can also be extracted from raw biopsy image data. The feature vectors can be extracted using a second machine learning model, which can include a convolutional neural network (CNN) model. The CNN model may include, for example, comprises at least one of: VGG (Visual Geometry Group), ResNet (Residual Neural Networks), DenseNet (Dense Convolutional Network), GAN (Generative Adversarial Network), etc. In some examples, at least some parameters of the CNN model are obtained based on transfer learning techniques, in which the weights of the lower level layers of the CNN model are developed for other tasks (e.g., to identify a boundary, to identify a shape, etc.), whereas the weights of the higher level layers of the CNN model are trained to use the outputs of the lower level layers to identify image features of tissues and cells which can include biomarkers useful for predicting a patient's response to a treatment. In some examples, the second machine learning model can be configured to process other types of images, such as radiology images.

As part of the extraction operation, the biopsy image data can be segmented into tissues of different types. Moreover, certain cells that can serve as biomarkers to measure a treatment response, such as lymphocytes, can be detected. The results of segmentation of biopsy image data, as well as the detection of lymphocytes and their locations, can become biopsy image feature data, which can be input to the trained machine learning model.

The clinical prediction may include predicting whether the patient is resistant or sensitive to a platinum drug treatment for a particular cancer type, a survival rate when receiving a particular treatment for a particular cancer type, etc. In some examples, the machine learning model can be generated/updated based on supervised learning techniques using labelled molecular data and labelled biopsy image data of a plurality of patients. The plurality of patients can include a first group of cancer patients who are sensitive to the a drug treatment and a second group of cancer patients who are resistant to the drug treatment. The machine learning model can be trained to, for example, compute a score by inputting the biopsy image data features and the molecular data features, with the parameters of the machine learning model obtained from a training process using the labelled molecular data and labelled biopsy image data to maximize a likelihood of making a correct prediction.

In some examples, the machine learning model can be generated/updated based on unsupervised learning techniques. For example, correlation values between molecular data features and biopsy image features can be computed, and pairs of molecular data feature and biopsy image feature that are highly correlated can be identified. Those highly correlated molecular data features and biopsy image features of a patient pool can be categorized into groups based on their values, and patients having the molecular data features and biopsy image features falling in each group can be identified into cohorts. A clinical prediction can be made for a new patient based on which group the molecular data features and biopsy image features of the new patient falls into, and the treatment responses of the patient cohort identified with the group.

With the disclosed embodiments, a machine-learning (ML) based clinical predictor can predict the response of a patient to a treatment based on the patient's molecular data and biopsy data, which may provide known or hidden information of the patient, such as pathological information, biological information, etc., that can determine the patient's response to the treatment. Moreover, via various supervised and unsupervised machine learning techniques, the predictor can learn about the molecular data and biopsy data of other patients and their treatment responses and refine the prediction based on the learning. With embodiments of the present disclosure, prediction of a patient's response to treatment can be made more accurately and earlier in the patient journey, and a corrective action, such as consideration of additional therapeutic options, available clinical trials, etc., can also be performed earlier. All these can increase the odds of recovery and survival of the patient.

I. Patient Treatment Response Analysis Over Time

Figure 1B:
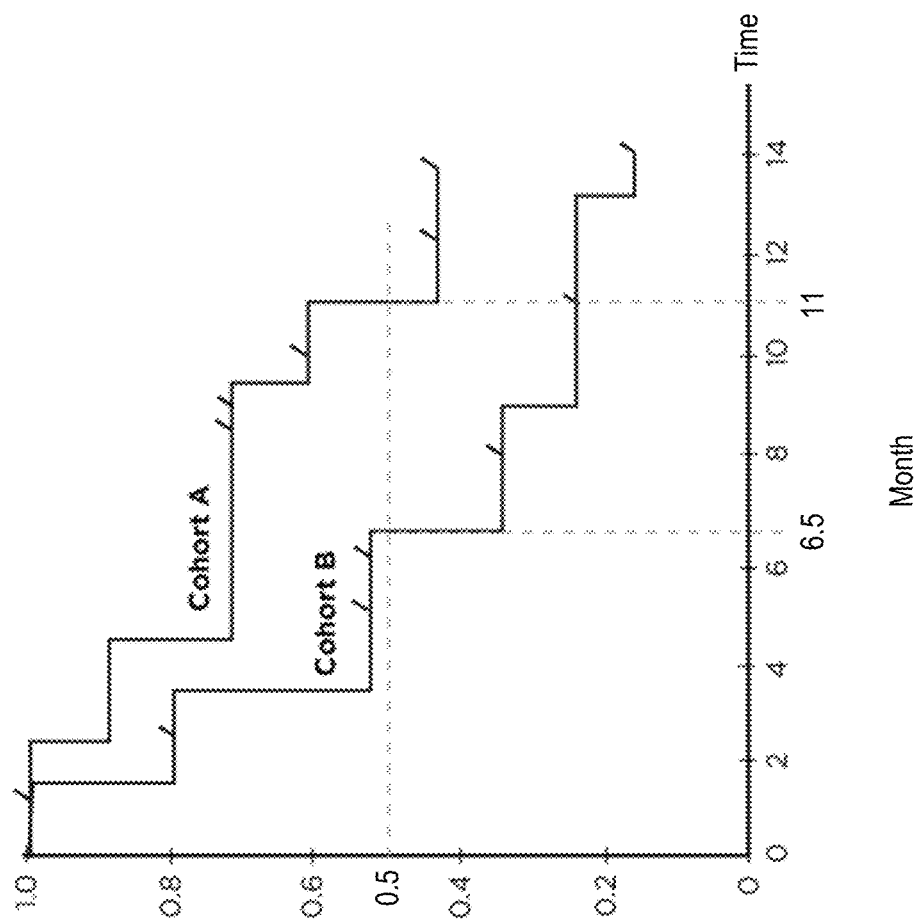

FIG. 1A and FIG. 1B illustrate example mechanisms for analyzing a patient's response to a treatment over time. FIG. 1A is a chart 100 illustrating an example timeline for determining whether a patient is sensitive or resistant to platinum drug treatment for ovarian cancer. As shown in FIG. 1, a patient may be diagnosed of having ovarian cancer at time T0. The patient may start receiving platinum drug treatment at time T1, and stop the platinum drug treatment at time T2. There are a number of possible outcomes of the platinum drug treatment. For example, the primary tumor of the patient may recur or progress between times T1 and T2 during the administration of platinum drug treatment. The primary tumor of the patient may also recur or progress within a 180-day period between time T2, when the platinum drug treatment ends, and time T3. In both cases, it can be concluded that the patient is resistant to the platinum drug treatment. On the other hand, if the primary tumor of the patient does not recur or progress between times T2 and T3, or after time T3, it can be concluded that the patient is sensitive to the platinum drug treatment. Moreover, if the primary tumor of the patient recurs or progresses after time T3, it can also be concluded that the patient is sensitive to the platinum drug treatment.

FIG. 1B is a chart 150 illustrating an example of a Kaplan-Meier (K-M) plot, which provides a study of survival statistics among patients having a type of cancer (e.g., lung cancer) who receive a treatment. A K-M plot shows the change of survival rate of a group of patients who receive a particular treatment with respect to time. As the time progresses, some patients may experience death, and the survival rate decreases. Some other patients can be censored (dropped) from the plot due to other events not related to the studied event, and those unrelated events are represented by ticks in the K-M plot. The length of each horizontal line represents the survival duration for that interval, and all survival estimates to a given point represent the cumulative probability of surviving to that time.

As shown in FIG. 1B, the survival rates of different cohorts A and B of patients (e.g., cohorts of patients having different characteristics, receiving different treatments, etc.) can be plotted in different K-M plots of chart 150. From FIG. 1B, the median survival (50% of patients would be estimated to be surviving) in cohort A is about 11 months, whereas in cohort B is about 6.5 months. K-M analysis is commonly reported with a hazard ratio, which expresses the chance (or hazard) of an event occurring in a cohort of patients receiving a particular treatment. A low hazard ratio can indicate a higher survival rate in the cohort compared with another cohort of patients who receive a different treatment (or no treatment).

II. Clinical Prediction

Figure 2:
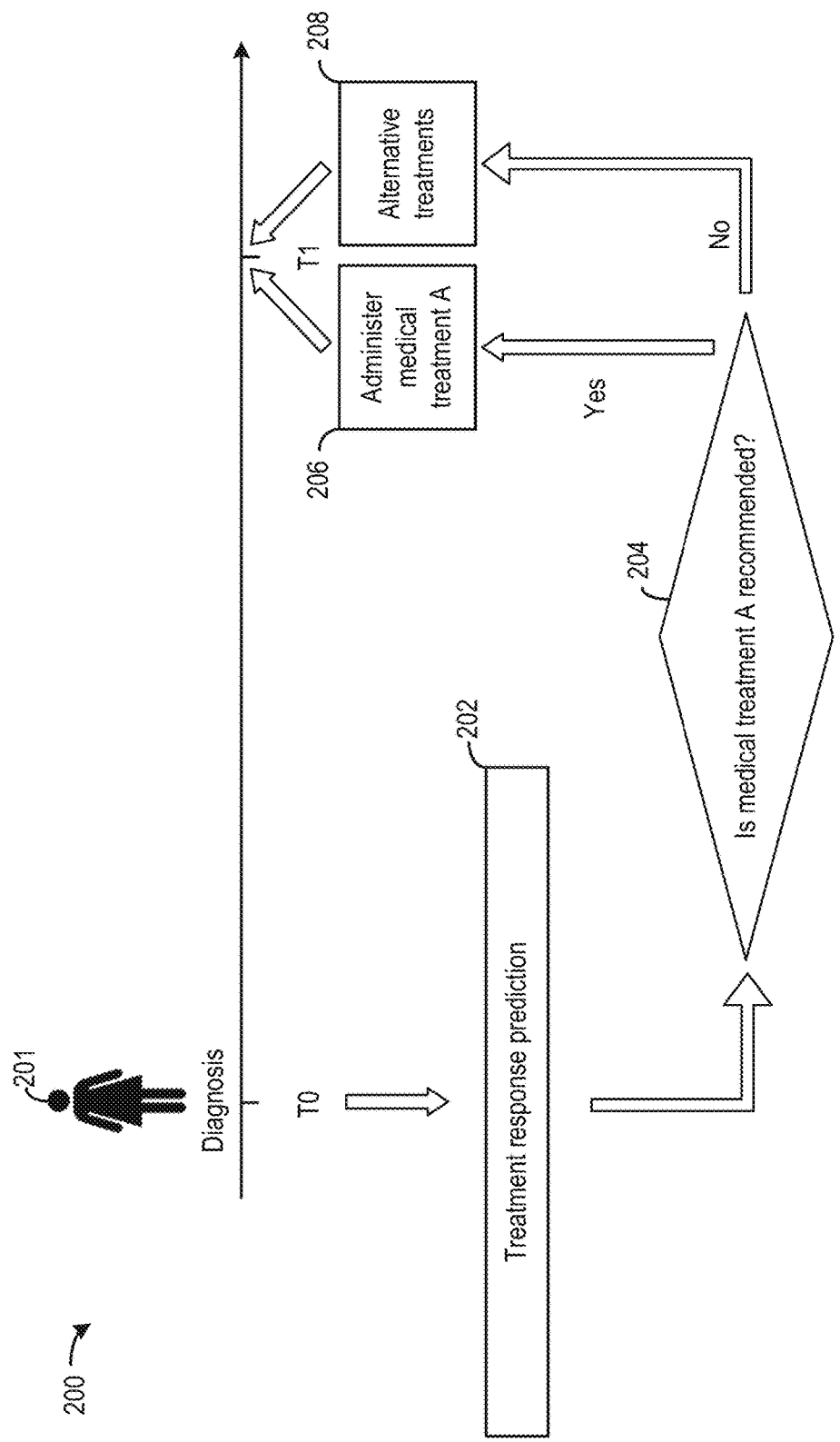
FIG. 2 illustrates an improved method of administering a medical treatment.

FIG. 2 illustrates a chart 200 illustrating an improved method of prediction of platinum drug treatment response, and performing a treatment based on the prediction. As shown in FIG. 2, a patient 201 is diagnosed to have a cancer (e.g., ovarian cancer, lung cancer, etc.) at time T0.

At block 202, a treatment response prediction can be performed to predict the response of patient 201 to medical treatment A. The treatment response prediction can be performed before starting a medical treatment A (e.g., a platinum treatment, an immunotherapy, a chemotherapy, etc.) at time T1. Based on the prediction, it can be determined whether medical treatment A is recommended. The prediction may include, for example, whether the patient will be responsive or resistant to medical treatment A, a predicted survival rate of the patient, whether medical treatment A will make a difference to the predicted survival rate of the patient, etc.

At block 204, where medical treatment A is recommended for patient 201 is determined, based on the prediction of the response of patient 201 to medical treatment A at block 202.

At block 206, if medical treatment A is recommended for patient 201 (at block 204), a health care provider can administer medical treatment A.

At block 208, if patient 201 is predicted to be resistant to medical treatment A (at block 204), the health care provider (or other health care provider) can administer alternative medical treatments such as, for example, a different medical treatment from treatment A, enrolling patient 201 in other clinical trials of new medications, etc.

Both the administration of medical treatment A (at block 206) and the administration of an alternative treatment (at block 208) can occur at time T1, as shown in FIG. 2, or they can occur at different times.

With the arrangements shown in FIG. 2, patient 201 can make a decision on whether to start a treatment or to use a different treatment at an earlier time. The time gained from making the decision early can be critical in halting the growth of the primary tumor and the spread of tumor cells to other organs. Being able to accurately predict a patient's response to a medical treatment can reduce the time wasted on a medical treatment that is not helpful to the patient, and can significantly increase the patient's odds of recovery and survival.

III. Apparatus for Performing Clinical Prediction

A clinical prediction apparatus can be used to perform a clinical prediction for a patient based on certain biological samples of the patient including molecular data and biopsy image of the patient. In a case where the clinical prediction is to predict whether the patient will be sensitive or resistant to a platinum drug treatment, the biopsy image can include biopsy image of a primary tumor at the patient. An example clinical prediction system is described below.

Figure 3:
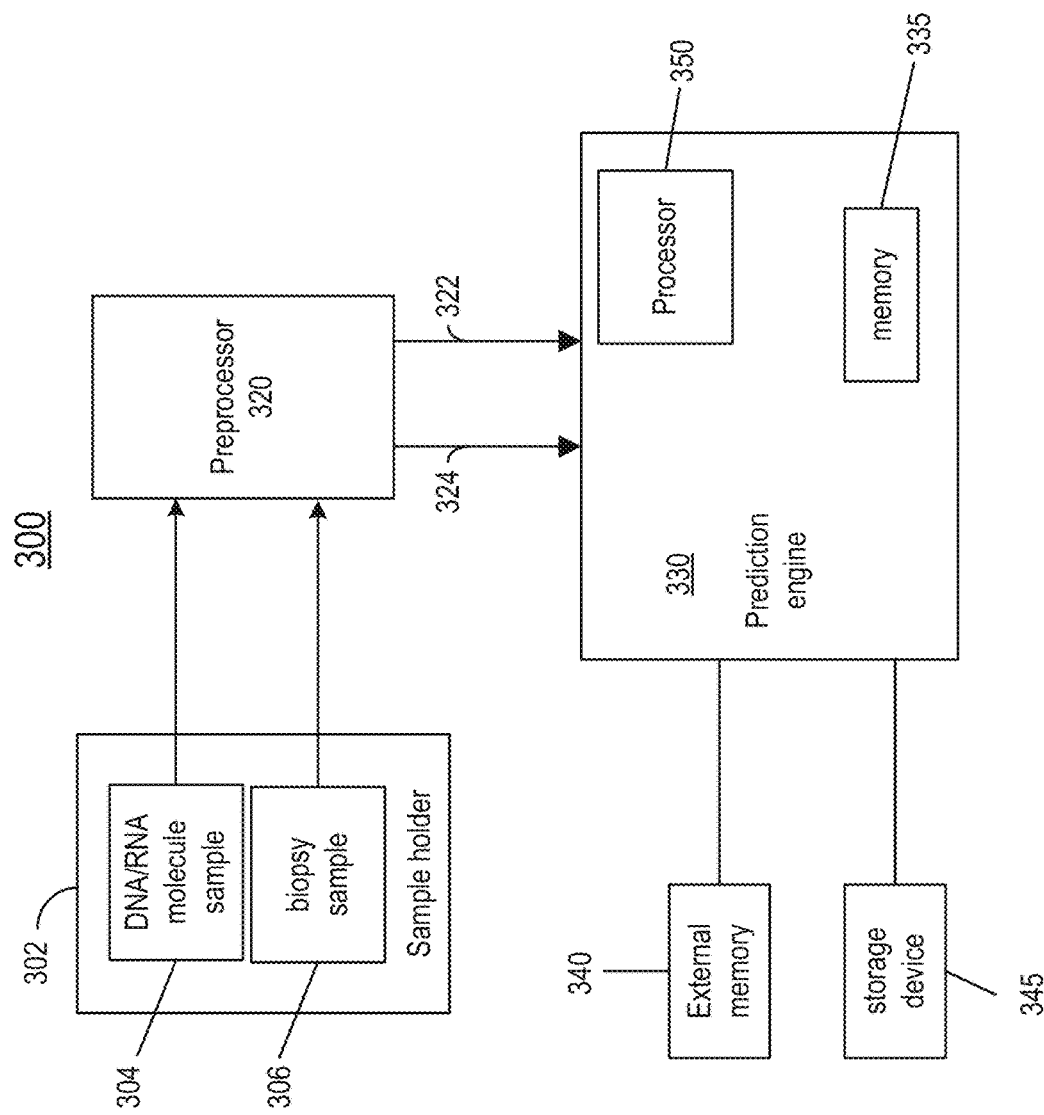
FIG. 3 illustrates a clinical prediction system according to an embodiment of the present invention, according to certain aspects of this disclosure.

FIG. 3 illustrates a clinical prediction system 300 according to an embodiment of the present invention. Clinical prediction system 300 can be used to perform the example clinical prediction as described in FIG. 2. System 300 as shown includes a sampler holder 302 that can hold input samples of a patient (e.g., patient 201), which include a deoxyribonucleic acid (DNA) molecule sample 304, such as a DNA molecule(s), and a biopsy sample 306, such as top and bottom frozen slides of a primary tumor tissue sample. DNA molecule sample 304 and biopsy sample 306 can be sent to preprocessor 320 to perform pre-processing. In some examples, preprocessor 320 can extract molecular data 322 from DNA molecule sample 304. In some examples, molecular data 322 may include, for example, RNA-seq, miRNA-seq, DNA methylation data, copy number variations (CNV) data, etc. Some of these data, such as RNA-seq and miRNA-seq., can be further processed to produce data tables which can map normalized values to genes. In addition, preprocessor 320 can include imaging devices to obtain biopsy images of biopsy sample 306.

Preprocessor 320 can also stain biopsy sample 306 with hematoxylin and eosin (H&E) to stain the otherwise transparent cell structures with a color (e.g., red, pink, etc.). The stained biopsy sample 306 can be imaged to obtain H&E histopathology images data 324 of biopsy sample 306. Notice that H&E staining is just an example. Other techniques of processing (e.g., staining with a different chemical, or no staining at all) can be performed on the biopsy samples prior to the imaging operation.

Molecular data 322 and H&E histopathology images data 324 can be sent to a prediction engine 330, which can perform a clinical prediction for the patient based on the data. Prediction engine 330 may include a processor 350 and a memory 335. Molecular data 322 and H&E histopathology images data 324 may be stored locally in prediction engine 330 in memory 335, or externally in an external memory 340 or a storage device 345. Prediction engine 330 may also include a set of instructions stored in memory 335 to be executed by processor 350 to perform the clinical prediction. Prediction engine 330 can predict, based on molecular data 322 and H&E histopathology images data 324, whether the patient will be sensitive or resistant to a platinum drug treatment. In some embodiments, prediction engine 330 can generate an output (e.g., for a display, for an audio speaker, etc.) to indicate a prediction result, to enable the patient and/or a health care provider to make a decision on whether to receive/administer the platinum drug treatment. In some embodiments, prediction engine 330 can be coupled with a medication administration system to control the administration of platinum drug treatment based on the prediction result. For example, if the prediction result indicates that the patient will be resistant to the platinum drug treatment, prediction engine 330 can disable the administration of the platinum drug treatment to the patient.

IV. Machine-Learning Based Clinical Predictor

Figure 4A:
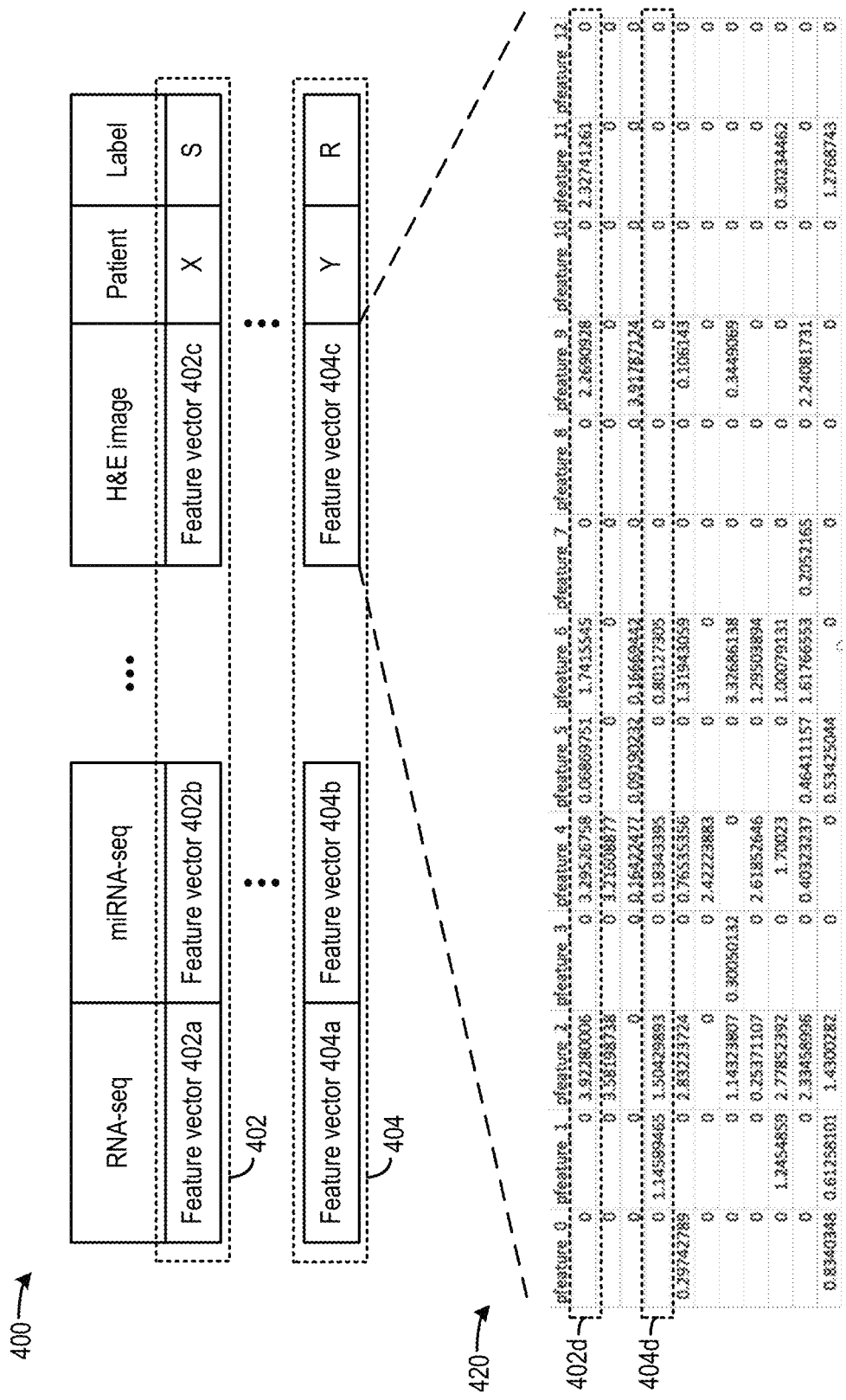
Figure 4B:
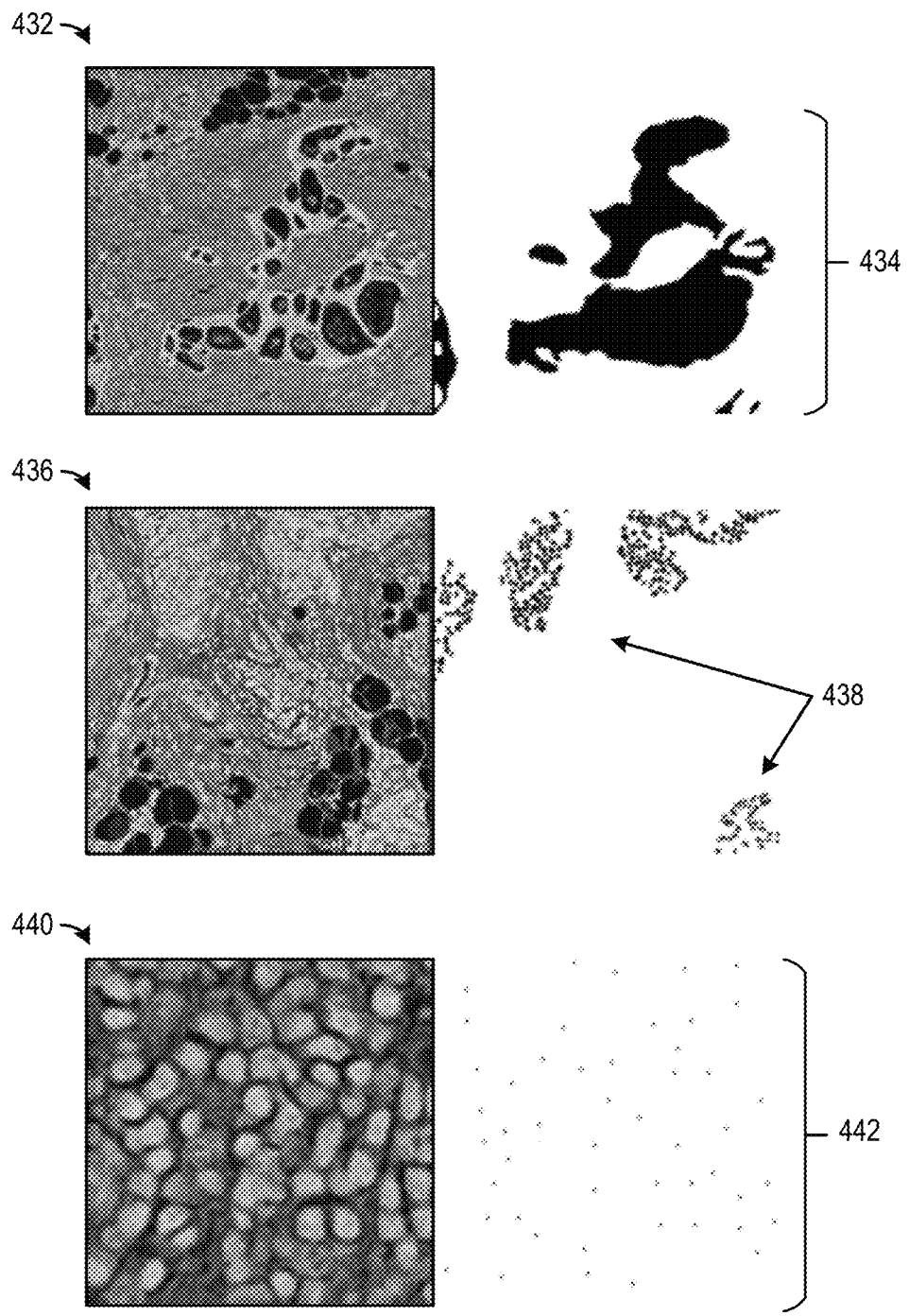
Figure 4C:
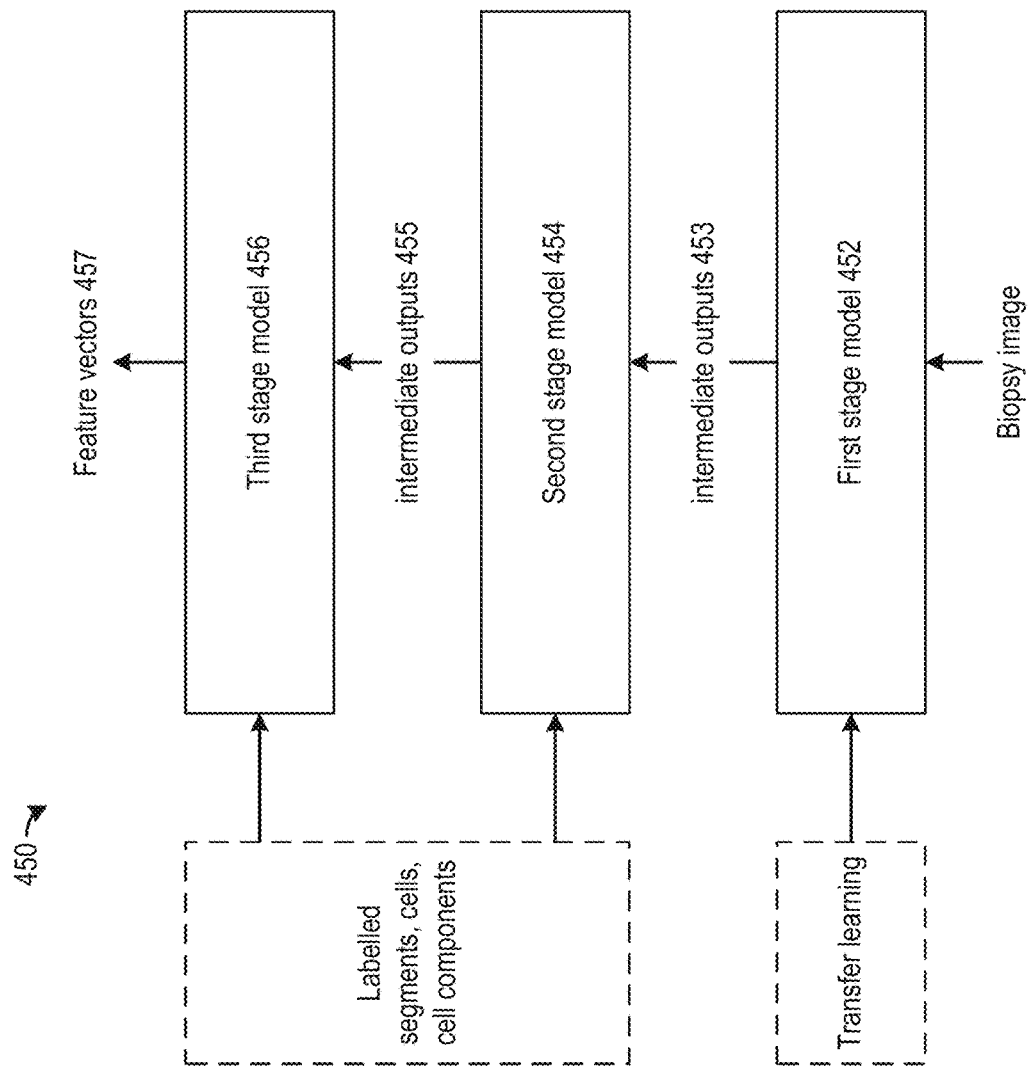
Figure 4E:
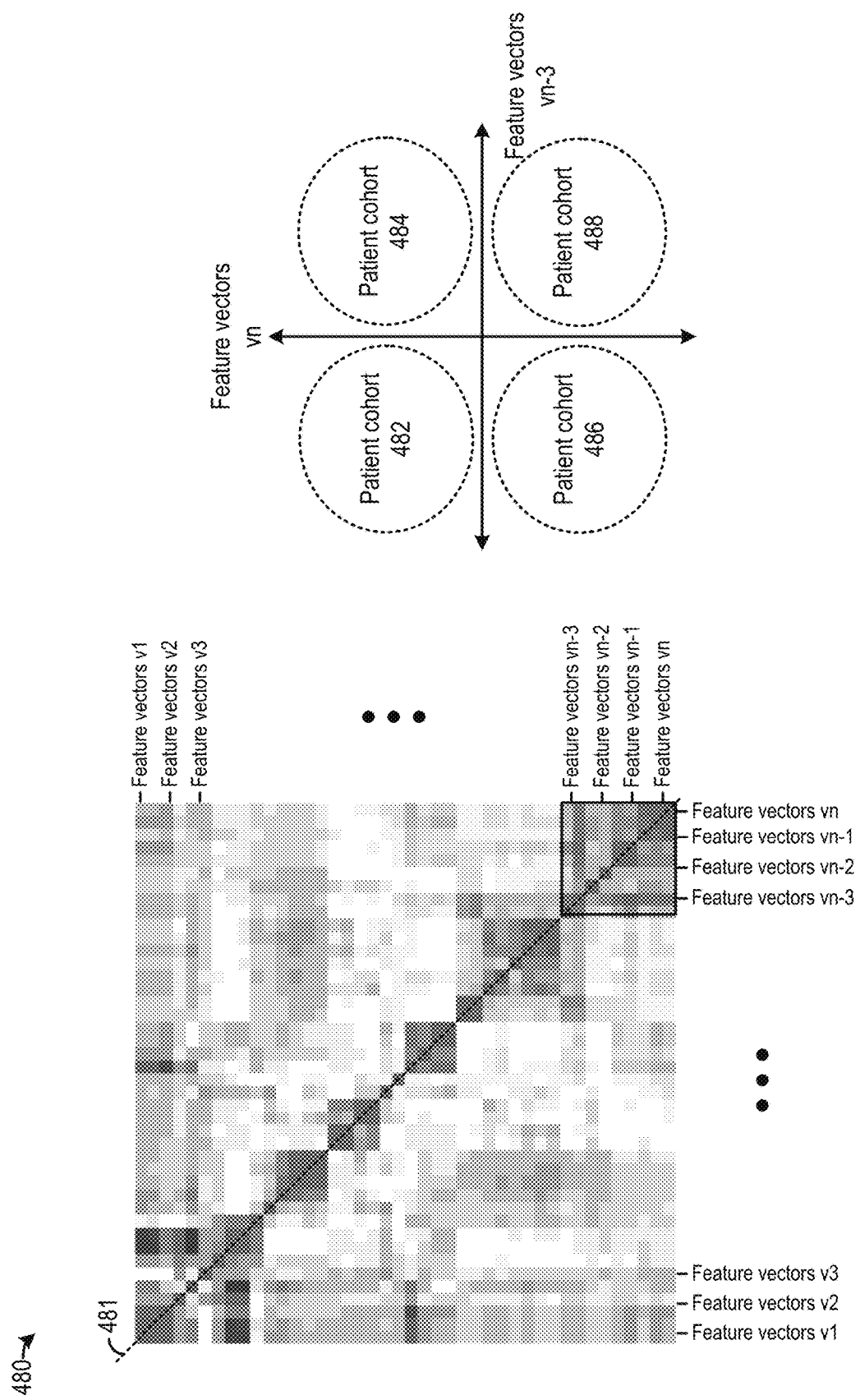

In some embodiments, prediction engine 330 may include a machine learning (ML) model to perform the prediction. In some examples, the machine learning model can include a set of model parameters that can be used to compute, for example, a score that indicates a likelihood of a patient being resistant or sensitive to a drug treatment, based on features of multi-modal data of the patient including molecular data and biopsy image data. In some examples, the machine learning model can identify highly correlated features among the multimodal clinical data and perform the prediction for a patient based on those features. FIG. 4A and FIG. 4B illustrate examples of features, whereas FIG. 4C, FIG. 4D, and FIG. 4E illustrate examples of machine learning models to process the multimodal features to make a prediction.

Referring to FIG. 4A, table 400 shows each modality of data (e.g., RNA-seq, miRNA-seq, H&E histopathology image data, etc.) of each patient can be represented by a feature vector. The data can be obtained from a primary tumor and other tissues of the patient. In one example, the data can be obtained from ovarian primary tumor samples with their corresponding H&E histopathology image data and RNA-seq and miRNA-seq. For example, a patient X may have a set of feature vectors 402 from multimodal clinical data comprising feature vector 402a of RNA-seq, feature vector 402b of miRNA-seq, feature vector 402c of H&E image, etc. A patient Y may have a set of feature vectors 404 comprising feature vector 404a of RNA-seq, feature vector 404b of miRNA-seq, feature vector 404d of H&E image, etc., which can have different vector values from the set of feature vectors 402 of patient X.

In some examples, feature vectors 402 and 404 can be used to train a machine learning model using supervised learning techniques. In such a case, each set of feature vectors 402 and 404 can further be associated with a label to indicate the patient's response to a treatment. For example, "R" may indicate the patient being resistant to the treatment, whereas "S" may indicate the patient being responsive to the treatment. Each feature vector in table 400 can be a numerical vector. Table 420 shows example of numerical feature vectors of H&E image, including feature vector 402d of patient X and feature vector 404d of patient Y. In table 420, the numeric values of feature vectors of the H&E image can represent pixel intensities. In other examples, the numeric values of feature vectors of the H&E image can represent other information derived from the pixel intensities including, for example, a count of certain types of cells (e.g., lymphocytic cell counts, epithelial cell counts, etc.), the spatial localization of the cells, the densities of the cells, etc.

FIG. 4B illustrates examples of features extracted from H&E images. For example, from H&E image 432, a tissue segmentation operation can be performed as part of the feature extraction process. Tissue segmentation can partition an image into segments corresponding to different tissue classes. In healthy subjects, these classes are biologically defined as specific types of tissue, whole organs, or sub-regions of organs (e.g., liver or lung segments or muscle groups). In patients, areas with pathologies such as tumors or inflammation can also be relevant for segmentation. A machine learning model (e.g., a neural network, such as CNN) can be trained with pixel data of images having segments labelled as part of a tissue class (e.g., an organ, part of an organ, a cell, a tumor, etc.).

The trained CNN can then process H&E image 432 to identify, for example, the boundary of tissue 434, the shape and size of tissue 434, the location of tissue 434, etc. In addition, different cells and their components can also be identified from the H&E image. For example, from H&E image 436, nuclei 438 of living cells can be identified, whereas from H&E image 440, lymphocyte cells 442 can be identified. The identification of cells and cell components can also be based on a CNN, which is trained with pixel data of images labelled/annotated to have the cells and/or cell components to be identified. In some examples, tissue segmentation, extraction of cells, and extraction of cell components can be part of a multi-stage feature extraction process performed by the machine learning model to compute image feature vectors.

FIG. 4C illustrates an example of a machine learning model 450 that can compute feature vectors from a biopsy image. As shown in FIG. 4C, machine learning model 450 can include a first stage model 452, a second stage model 454, and a third stage model 456. Each of first stage model 452, second stage model 454, and third stage model can include a machine learning model such as CNN. First stage model 452 can receive pixel data of a biopsy image and perform lower-level image recognition tasks (e.g., to identify a boundary, to identify a shape, etc.) on the pixel data to generate intermediate outputs 453. Intermediate outputs 453 can indicate, for example, the identification of a boundary, a particular shape, etc. at different regions of the biopsy image.

Second stage model 454 can perform the aforementioned tissue segmentation operations, cell extraction operations, and/or cell component extraction operations based on intermediate outputs 453, to generate intermediate outputs 455. Intermediate outputs 455 can indicate, for example, a likelihood of each image region being part of a tissue of interest (e.g., a tumor, an organ, etc.), a likelihood of each image region having the cell of interest (e.g., a tumor cell, a lymphocytic cell, etc.), a likelihood of each image region having a cell component of interest (e.g., cell nuclei, etc.), etc. Third stage model 456 can perform additional processing of intermediate outputs 455 to compute feature vectors 457 representing, for example, a count of certain types of cells (e.g., lymphocytic cell counts, epithelial cell counts, etc.), the spatial localization of the cells, the densities of the cells, etc.

Each of first stage model 452, second stage model 454, and third stage model 456 can be trained to perform the computations. The training can be based on labelled image data (e.g., image data labelled to include certain tissue segments, cells, cell components, etc.) to maximize the likelihood of learning model 450 outputting correct likelihoods of finding tissue/cell/cell component in different regions of the input biopsy image and hence generating feature vectors that correctly represent the biopsy image. In some examples, first stage model 452 can be trained/developed using transfer learning techniques, in which the parameters of first stage model 452 can originate from the training for a different image recognition operation (e.g., to recognize a cat, a dog, etc.), based on an assumption that the identification of tissues, cells, and cell components from a biopsy image involves common lower-level image recognition tasks as other image recognition operations. With such arrangements, the number of training process for first stage model 452, and for machine learning model 450 as a whole, can be reduced.

Figure 4F:
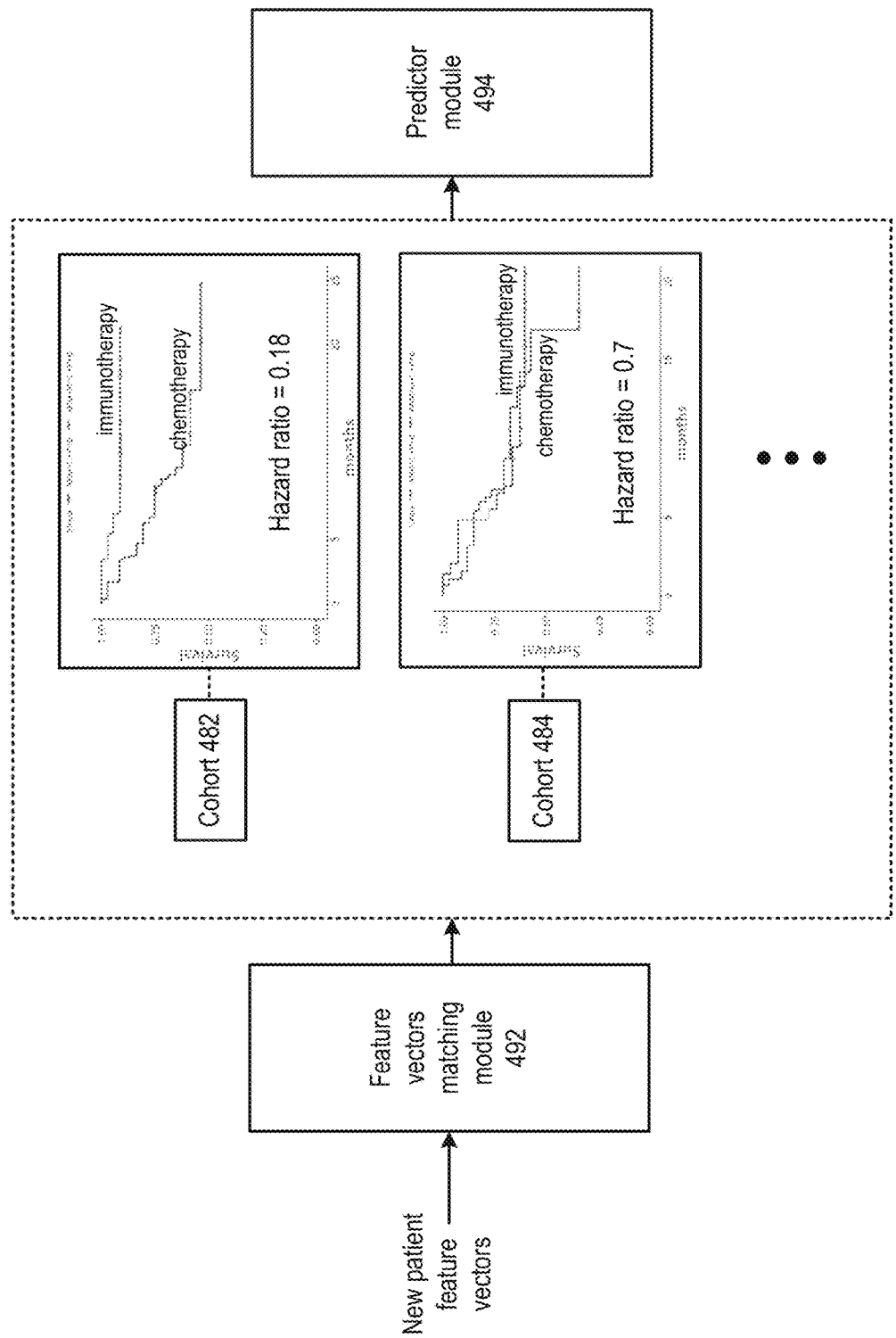

FIG. 4D, FIG. 4E, and FIG. 4F illustrate examples of machine learning models to process the multimodal features to make a prediction. As shown on the left side of FIG. 4D, in one example, each set of feature vectors of a modality of data (e.g., RNA-seq, miRNA-seq, protein expression, H&E histopathology image data, etc.) can represent a dimension in model space 460. The machine learning model may include a set of model parameters to represent a relationship between the feature vectors of each modality of data and a score that indicates a likelihood of the patient being sensitive (or resistant) to the drug treatment (e.g., platinum drug treatment). Each parameter may represent, for example, a contribution of the feature vector of each modality of data to the score. An example of such a relationship can be represented as follows:

$$\text{Score} = \alpha \times f_1(v_{RNA}) + \beta \times f_2(v_{miRNA}) + \gamma \times f_3(v_{protein}) + \delta \times f_4(v_{H\&E}) \quad \text{(Equation 1)}$$

In equation 1, $f_1$ can represent a first mathematical function that accepts the feature vector of RNA-seq ("$v_{RNA\text{-}seq}$") to generate a first output, $f_2$ can represent a second function that accepts the feature vector of miRNA ("$v_{miRNA\text{-}seq}$") to generate a second output, $f_3$ can represent a third function that accepts the feature vector of protein expression ("$v_{protein}$") to generate a third output, whereas $f_4$ can represent a fourth function that accepts the feature vector of H&E image ("$v_{H\&E}$") to generate a fourth output. Each of the first output, second output, third output, and fourth output can be scaled by, respectively, a first scaling factor α, a second scaling factor β, a third scaling factor γ, and a fourth scaling factor δ. A score can be computed based on a sum of the scaled first, second, third, and fourth outputs. The score can represent, for example, a percentage value indicating a likelihood that the patient is sensitive to the platinum drug treatment for ovarian cancer, or other treatments for other cancers. If the score is equal to or exceeds a threshold, prediction engine 330 can output a prediction that the patient will be sensitive to the platinum drug treatment. If the score is below the threshold, prediction engine 330 can output a prediction that the patient will be resistant to the platinum drug treatment.

A. Example for Supervised Learning

Various machine learning models can be used to perform the computations of Equation 1 in prediction engine 330. The right side of FIG. 4D illustrates an example of a multilayer neural network 470 that can perform the computation and prediction. It is understood that prediction model 103 can also include other different types of neural networks including, for example, long short-term memory (LSTM), multilayer perception (MTP), multiscale densenet (MSD-NET), etc. As shown in FIG. 4D, neural network 470 may include multiple neural network layers including an input layer 472, a middle layer 474, and an output layer 476. Each neural network layer includes a plurality of processing nodes, with each processing node configured to perform operations representing a neuron operation.

Each processing node of input layer 472 can receive a feature vector (e.g., one of feature vectors 402a-402d) of a patient and scale the feature vector with a corresponding weight from weight matrix W1. The weight can represent (or be part of) the scaling factors in Equation 1 and can determine the influence of the feature vector to the final prediction output. Each node in middle layer 474 can receive the scaled feature vectors from each node of input layer 472 and generate an intermediate output. For example, the intermediate output from node 474a (intermediate$_{474a}$) can be generated based on the following equation:

$$\text{intermediate}_{474a} = \Sigma_{i=0}^{n}(W1_i \times x_i) \quad \text{(Equation 2)}$$

In Equation 2, $W1_i \times x_i$ represents a scaling of a particular feature vector (e.g., $x_0$) with the associated weight (e.g., $W1_0$). The sum may also represent a dot-product between the feature vectors and a weight vector. In some examples, a bias can also be added the scaled outputs to generate the intermediate output.

Each node of middle layer 474 can further scale the intermediate output by a weight from weight matrix W2. The scaled intermediate outputs can then be forwarded to output layer 476 which, in neural network 470, may include only one node. Output layer 476 can sum the scaled intermediate outputs based on Equation 2 to generate the score of Equation 1. After generating the score, output layer 476 can generate a prediction output by processing the score with an activation function, which can be analogous to the firing of a biological neuron. An example of the activation function can be a rectified linear unit (ReLU) defined according to the following equation:

$$ReLU(x) = \begin{cases} x & \text{for } x \geq 0 \\ 0 & \text{for } x < 0 \end{cases} \quad \text{(Equation 3)}$$

In addition to ReLU, other forms of activation function can also be used including, for example, a softplus function (which can be a smooth approximation of a ReLU function), a hyperbolic tangent function (tanh), an arc tangent function (arctan), a sigmoid function, a Gaussian function, etc.

Output layer 476 can apply the ReLU function on the score based on the following Equation:

$$\text{prediction output} = ReLU(\text{score}) \quad \text{(Equation 4)}$$

Output layer 476 can then compare the prediction output with a threshold. If the prediction output meets or exceeds a threshold, output layer 476 can output an indication that the patient is likely to respond to the treatment, whereas if the prediction output is below the threshold, output layer 476 can output an indication that the patient is unlikely to respond to the treatment.

The parameters of the machine learning model, such as scaling factors α, β, γ, and δ, parameters of function $f_1$, $f_2$, $f_3$, $f_4$, etc., as represented by weight matrices W1 and W2, can be obtained by a supervised training process, in which the machine learning model can be provided with the feature vectors of the labelled molecular data and labelled biopsy image data of other patients who also had ovarian cancer and had received the platinum drug treatment at time T1, and the parameters can be modified by the training process to maximize a likelihood that the machine learning model correctly predicts the resistant/sensitive outcome of those other patients.

The patients can be divided into two group—a first group who turned out to be sensitive to the platinum drug treatment, and a second group who turned out to be resistant to the platinum drug treatment. Referring back to FIG. 1A, the first group, labelled as sensitive, might show no recurrence or progression of the primary tumor within the 180-day period between times T2 and T3, or recurrence or progression of the primary tumor after time T3. The second group, labelled as resistant, might show recurrence or progression of the primary tumor within times T1 and T2, or within the 180-day period between times T2 and T3. The multi-modal data for each group of patients can be collected at time T0. The multi-modal data of each patient can be stored in table 400, and associated with the label of the patient (sensitive or resistant).

The parameters of the machine learning model, such as the weights of neural network 470, can be updated in the training process to maximize the likelihood of the machine learning model generating, based on labelled multi-modal data of table 400, a prediction output that matches the label of those data. For example, the parameters of the machine learning model can be updated in the training process to maximize the likelihood of predicting, when receiving the labelled multi-modal data as inputs, that the first group of patients is sensitive to the platinum drug treatment and that the second group of patients is resistant to the platinum drug treatment. Upon training the machine learning model, the feature vectors of a patient's molecular data and biopsy image data (of the same modals as the labelled multi-modal data) can be input to the machine learning model to generate a prediction.

B. Example for Unsupervised Learning

FIG. 4E and FIG. 4F illustrate another example of a machine learning model that can be used to perform clinical prediction in prediction engine 330. In the examples of FIG. 4E and FIG. 4F, a machine learning model can be generated/updated based on unsupervised learning techniques, such as linear regression. On the left of FIG. 4E is a graph 480 that illustrates a plot of correlation values between pairs of feature vectors among the patients. In graph 480, diagonal 481 represents the autocorrelation of each feature vector and is the highest among all the correlation values, whereas the correlation values between pairing of different feature vectors are lower. In graph 480, it can be determined that correlation values of pairing of feature vectors vn, vn-1, vn-2, and vn-3 are the highest, which indicate that these feature vectors are highly correlated. In one example, these feature vectors can represent multimodal data including lymphocytic H&E image features and gene expressions of T cell markers, such as CD8A, TNF, CD4, EOMES, CTLA4, ICOS, CXCL10, and CD274.

As part of the machine learning model, the two (or multiple) feature vectors that have the highest correlation values among the feature vectors can be identified from graph 480. In the example of FIG. 4E, feature vector vn, which represents lymphocytic H&E image features, and feature vector vn-3, which represents a gene expression of T cell markers, can be identified. As shown on the right of FIG. 4E, based on the distribution of the different magnitude values of feature vectors vn-3 and vn, the feature vectors can be grouped into different quadrants, and the patients having feature vectors vn and vn-3 falling into each quadrant can be identified, and divided into cohorts, such as patient cohorts 482, 484, 486, and 488.

For each of patient cohorts 482, 484, 486, and 488, a statistical survival rate analysis, such as Kaplan-Meier (K-M) analysis and the corresponding hazard ratio can be performed. The ranges of the feature vectors vn and vn-3 for each patient cohort, as well as the patient cohort's corresponding hazard ratio for two or more alternative treatments (e.g., immunotherapy, chemotherapy, etc.), can be used to create a machine learning model 490 to perform a clinical prediction.

Specifically, referring to FIG. 4F, machine learning model 490 can include a feature vectors matching module 492 to identify which patient cohort a new patient belongs based on matching the new patient's feature vectors vn and vn-3 with the ranges of those feature vectors for each patient cohort. Machine learning model 490 further includes a predictor module 494 which can, based on identifying the cohort, identify the hazard ratio of the cohort, and perform a prediction of the survival rate of the new patient for each of the alternative treatments based on the hazard ratio.

In the example of FIG. 4F, if machine learning model 490 determines that the new patient is in patient cohort 482, it can determine that the survival rate of the new patient can be boosted considerably by undergoing immunotherapy treatment instead of chemotherapy treatment based on the low hazard ratio (0.18). But if machine learning model 490 determines that the new patient is in patient cohort 482, it can determine that the survival rate is not boosted by either immunotherapy treatment or chemotherapy treatment based on the high hazard ratio (0.7), and may generate either no recommendation or recommend something else other than immunotherapy and chemotherapy.

Machine model 490 can be continuously updated based on feature vectors of new patients and their responses to the treatments. For example, as part of the updating, new feature vectors that are highly correlated can be identified and grouped. New patient cohorts can be regenerated based on the new feature vectors, and new K-M analyses and hazard ratios can be regenerated for the new patient cohorts.

C. Example System to Update the Machine Learning Based Clinical Predictor

Figure 5:
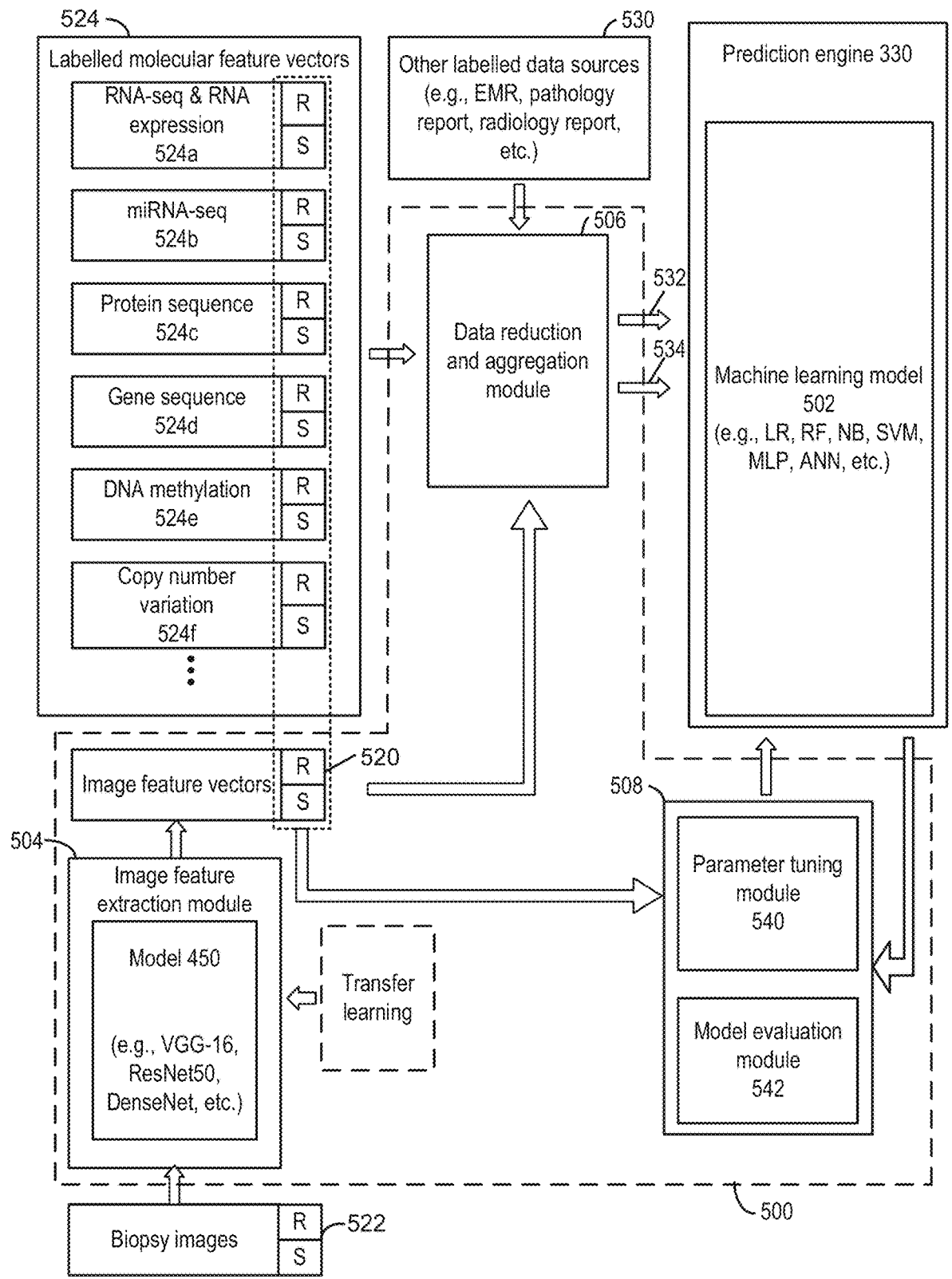
FIG. 5 illustrates a configuration module for configuring a machine learning model to perform a prediction, according to certain aspects of this disclosure.

FIG. 5 is a block diagram of a configuration module 500 according to an embodiment of the present invention. In some examples, configuration module 500 can perform training on a machine learning model 502 (e.g., neural network 470 of FIG. 4D) of prediction engine 330 using supervised learning techniques, as described above. In some examples, configuration module 500 can also update machine learning model 502 (e.g., machine learning model 490 of FIG. 4E) of prediction engine 330 using unsupervised learning techniques. In addition, configuration module 500 can also perform evaluation of machine learning model 502 and, based on a result of the evaluation, instructs prediction engine 330 to select a different machine learning model for the prediction. Configuration module 500 can include software instructions and can be executed by a hardware processor. In some embodiments, configuration module 500 can be part of clinical prediction system 300 and executed on processor 350. In some embodiments, configuration module 500 can also be external to clinical prediction system 300. As shown in FIG. 5, configuration module 500 includes an image feature extraction module 504, a data reduction and aggregation module 506, and a training and evaluation module 508.

Image feature extraction module 504 can extract image feature vectors 520 from labelled biopsy images data 522, which can include H&E histopathology images data 324 of FIG. 3. As shown in FIG. 5, image feature extraction module 504 may include machine learning model 450 of FIG. 4C, which can include, for example, a CNN. Various types of CNN can be used including, for example, VGG (e.g., VGG-16), ResNet (e.g., ResNet-50), DenseNet, etc. Machine learning model 450 of FIG. 4C can be used to perform automated feature extraction from the biopsy images data. As described above, the models can be pre-trained to extract features from an image, and the parameters of part of machine learning model 450 (e.g., first stage model 452) are not trained/modified by configuration module 500 but rather are obtained from a different source (e.g., another training operation that trains first stage model 452 for a different image recognition operation). In some embodiments, certain pre-processing of biopsy images data 522 (e.g., file format conversion, file size reduction, etc.) can be performed, and the pre-processed biopsy images data 522 can be processed by machine learning model 450 to extract image feature vectors 522. In a case where supervised learning is used, image feature vectors 522 can be labelled (e.g., resistant or sensitive, represented by 'R' and 'S') based on the label of the corresponding biopsy images data 522.

In addition to generating image feature vectors 522, configuration module 500 also accepts labelled molecular feature vectors 524, which include, for example, RNA-seq and RNA expression feature vectors 524*a*, miRNA-seq feature vectors 524*b*, protein sequence feature vectors 524*c*, gene sequence feature vectors 524*d*, DNA methylation feature vectors 524*e*, copy number variation feature vectors 524*f*, etc., each of which is labelled (e.g., resistant or sensitive). In some embodiments, configuration module 500 may include extraction modules (e.g., using a machine learning model) to obtain labelled molecular data from a database (e.g., Cancer Genome Atlas (TCGA) Consortium 1, National Cancer Institute (NCI) Genome Data Commons 2 (GDC), etc., and extract feature vectors from the molecular data. In some embodiments, configuration module 500 may receive other labelled modal of data from other data sources 530 to perform the training and configuration process. For example, configuration module 500 may receive labelled data from electronic medical record (EMR), pathology report, radiology report, etc., for patients who were found to be sensitive (or resistant) to the platinum drug administration. The data are also in the form of feature vectors and can be included in the training and configuration process.

To speed up the training process, and to maintain the training data at an optimum granular level to improve the prediction accuracy of the machine learning model, data reduction and aggregation module 506 may perform dimension reduction processing on the input feature vectors (e.g., labelled image feature vectors 520, labelled molecular feature vectors 524, feature vectors from other data source 530, etc.). The dimension reduction may include removing certain feature vectors from the a modality of data (e.g., from miRNA sequence 524b, image feature vectors 520, etc.). The dimension reduction can be performed using various statistical techniques including, for example, analysis of variance (ANOVA), principal component analysis (PCA), etc.

In addition, data reduction and aggregation module 506 may also perform data aggregation. For example, data reduction and aggregation module 506 may sort through labelled molecular feature vectors 524 and image feature vectors 520, and determine a subset of molecular feature vectors 524 and a subset of image feature vectors 520 that have common owners, to build a table of feature vectors (similar to table 400 of FIG. 4) for each of these common owners. With such arrangement, a full set of feature vectors for each labelled patient (e.g., being resistant or sensitive) can be obtained and used to train machine learning model 502. Other operations, such as cross-validation, can also be performed to the feature vectors.

The dimension-reduced and merged feature vectors can be split into a test data set 532 and a training data set 534. Training data set 534 can be used to train machine learning model 502, whereas test data set 532 can be used to evaluate machine learning model 502 after the training. In some embodiments, the splitting can be based on a pre-determined ratio of volume of data (e.g., 75% of data is provided for training, and 25% of data is for testing).

Training and evaluation module 508 includes a parameter tuning module 540 and a model evaluation module 542. Parameter tuning module 540 can train update learning model 502 based on training data set 534 using supervised learning or unsupervised learning techniques as described in FIG. 4A-FIG. 4F. For example, parameter tuning module 540 can receive a set of labels of feature vectors included in training set 534, receive prediction outputs of machine learning model 502 based on processing training set 534, and tune the parameters (e.g., hyper parameters) of machine learning model 502 based on comparing the prediction outputs and the set of labels. The tuning of the parameters can be based on, for example, minimizing value of a loss function for the training set. Various techniques can be used for the training including, for example, Bayesian optimization, gradient-based optimization, random search, etc. As another example, parameter tuning module 540 can determine the correlation values of pairs of feature vectors and identify new feature vectors that are highly correlated. Parameter tuning module 540 can also generate new patient cohorts based on the new feature vectors, and generate new K-M analyses and the hazard ratios for the new patient cohorts to update machine learning model 502.

In addition, model evaluation module 542 can apply test data set 532 to evaluate the performance of machine learning model 502 based on predetermined criteria, such as AUC (area under curve) of a receiver operating characteristic (ROC) curve. For example, to evaluate machine learning model 502, model evaluation module 542 can supply test data set 532 (with or without scaling) to machine learning model 502 and obtain a plot between true positive rate (TPR) versus false positive rate (FPR), and determine the area under the plot. Model evaluation module 542 can repeat the evaluation for other candidate machine learning models based on test data set 532, and select a machine learning model to perform the prediction based on the result of evaluation.

Embodiments of the present disclosure can improve the accuracy of clinical prediction by leveraging potential correlations between multi-modal data (e.g., RNA sequence, miRNA sequence, H&E image features) and a patient's response to a medical treatment, even if those potential correlations are not fully understood at this point. Embodiments of the present disclosure also allow a prediction to be made based on combination of various modalities of data, instead of a single modality (e.g., based purely on H&E image features alone, RNA sequence alone, etc.), which can improve the accuracy of prediction. Moreover, embodiments of the present disclosure can further refine the ML based prediction by evaluating a set of candidate machine learning models and selecting a machine learning model to perform the prediction, to further improve the accuracy and reliability of the prediction. All these allows clinical prediction to be performed accurately, which can substantially improve the patient's odds of recovery and survival.

V. Method

Figure 6:
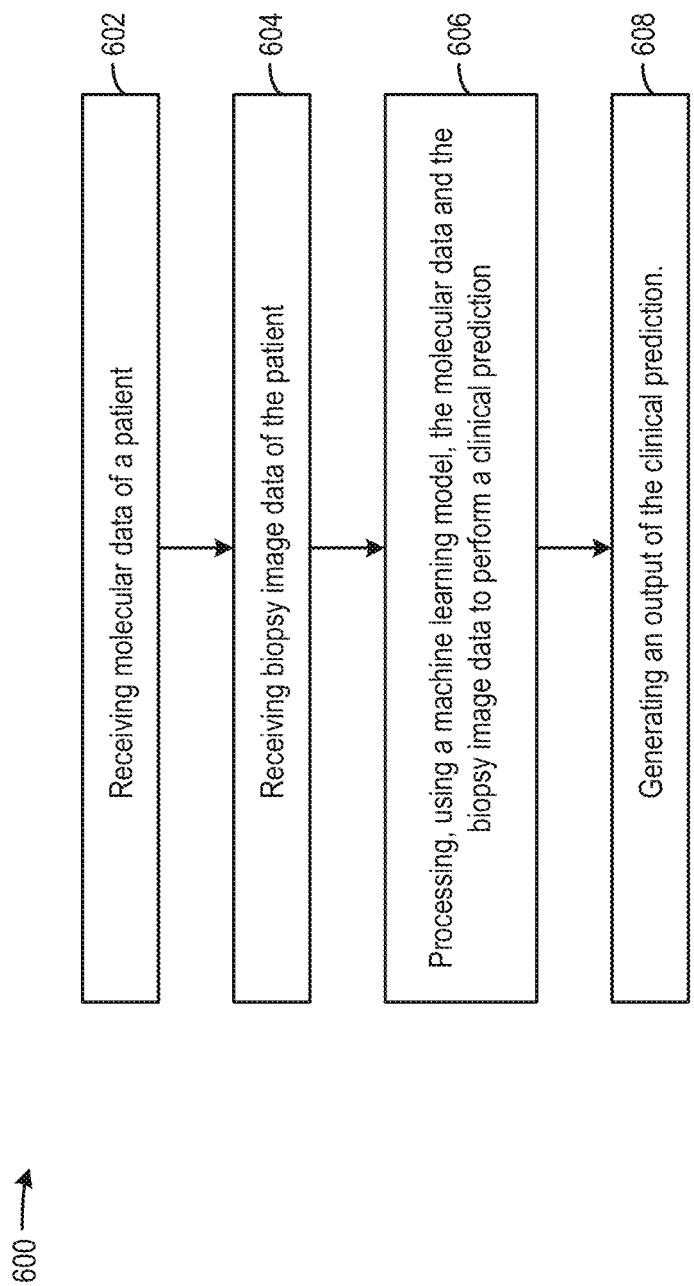
FIG. 6 illustrates a method of performing clinical prediction, according to certain aspects of this disclosure.

FIG. 6 illustrates a method 600 of performing a clinical prediction. The clinical prediction may include for example, predicting a response of the patient to a treatment for a disease, predicting a risk of the patient having the disease, etc. In some embodiments, the clinical prediction comprises predicting whether the patient is resistant or sensitive to a platinum drug treatment for ovarian cancer. Method 600 can be performed by, for example, one or more components of clinical prediction system 300, such as prediction engine 300, of FIG. 3.

At operation 602, prediction engine 300 may receive molecular data of a patient. The molecular data may include, for example, RNA sequences, RNA expression, one or more microRNA (miRNA) sequences, protein expression data, gene sequence data, DNA methylation data, or copy number variation (CNV) data, etc. The molecular data can be derived from DNA molecule samples of the patient. In some embodiments, the molecular data can be pre-posted (e.g., using a machine learning model) to extract feature vectors.

At operation 604, prediction engine 330 may receive biopsy image data of a patient. The biopsy image data may include biopsy image data of a primary tumor. The image can include, for example, hematoxylin- and eosin-stained (H&E) histopathology data.

At operation 606, prediction engine 330 may process, using a machine learning model, the molecular data and the biopsy image data to perform a clinical prediction. The machine learning model can include, for example, a neural network model (e.g., neural network model 470 of FIG. 4C), a machine learning model based on linear regression (e.g., machine model 490 of FIG. 4E), etc. In some examples, the machine learning model can be trained/updated based on based on labelled molecular data and labelled biopsy image data of a plurality of patients using a supervised learning technique. In some examples, the machine learning model can be updated/trained based on unlabelled molecular data and biopsy image data using an unsupervised learning technique. The training/updating of the machine learning model can be based on techniques as described in FIG. 4A-FIG. 4F and FIG. 5.

At operation 608, prediction engine 330 may generate an output of the clinical prediction. The output can be include display signals, audio signals, etc., to indicate a result of the prediction. In some embodiments, prediction engine 330 can also control a medication administration system to administer (or not to administer) the medication based on the result of prediction.

VI. Experimental Results

Figure 7A:
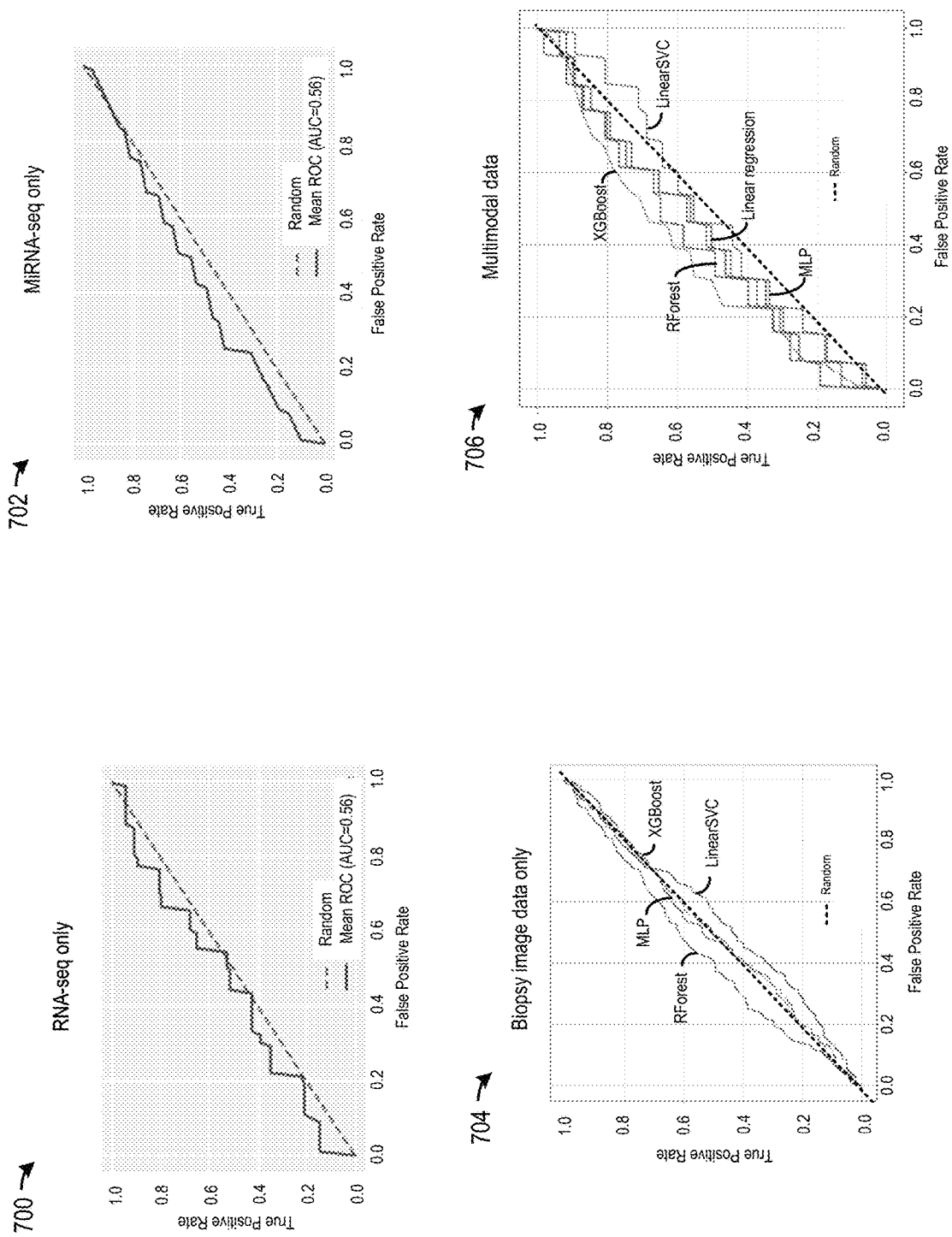
FIG. 7A, FIG. 7B, and FIG. 7C illustrate examples of experimental results of a clinical prediction system according to certain aspects of this disclosure.
Figure 7B:
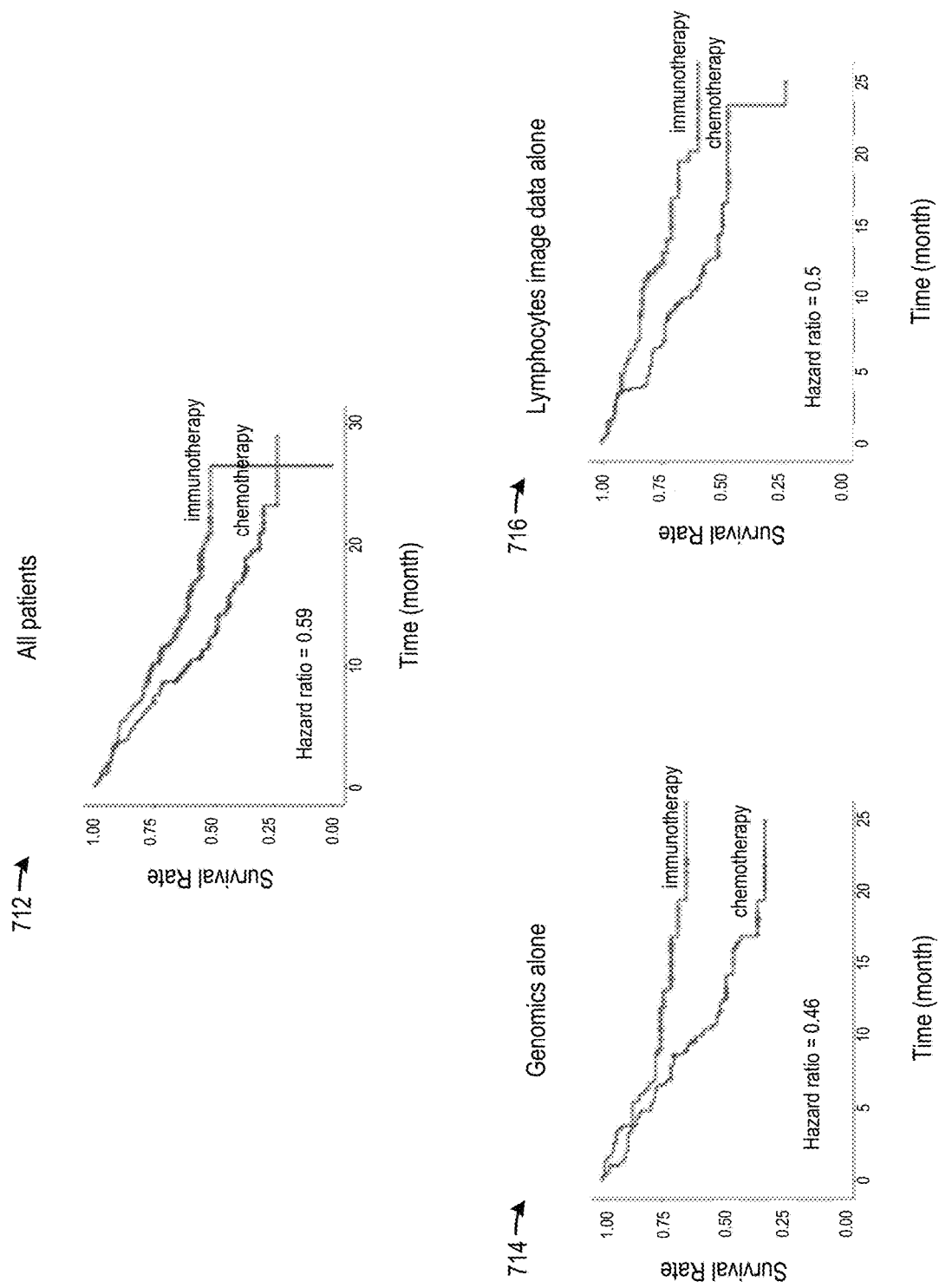
Figure 7C:
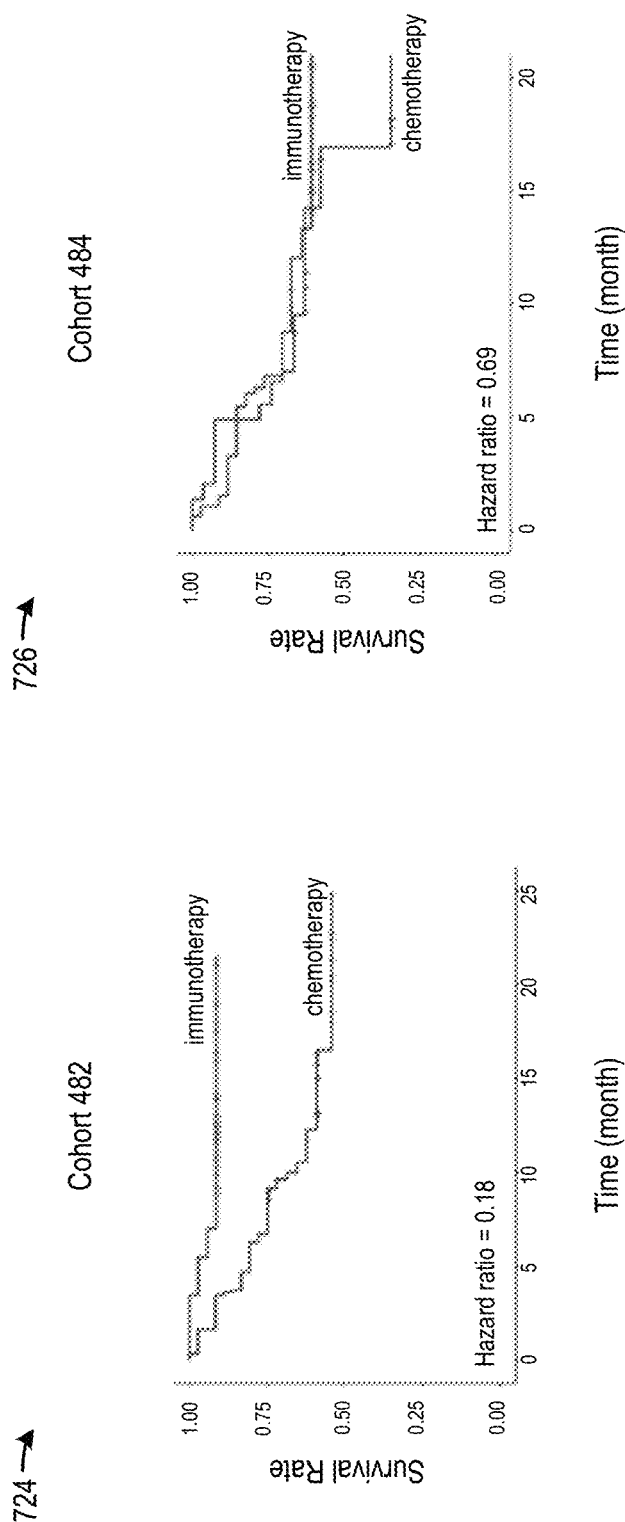

FIG. 7A, FIG. 7B, and FIG. 7C illustrate examples of experimental results achieved by embodiments of the present disclosure.

A. Experimental Results of Predicting a Platinum Drug Treatment Responses for Ovarian Cancer FIG. 7A illustrates receiver operating characteristic (ROC) plots 700, 702, 704, and 706. An ROC plot is a graphical plot that illustrates the diagnostic ability of a classifier system as its discrimination threshold is varied. An ROC plot is created by plotting the true positive rate (TPR) against the false positive rate (TPR) at different threshold settings. One performance metric of an ROC plot is area under curve (AUC) which represents the probability that a classifier will rank a randomly chosen positive instance higher than a randomly chosen negative one. An AUC value of 50% means the classifier's output is random. A higher AUC value (higher than 50%) can indicate that the classifier has a higher likelihood of generating the correct classification output.

In FIG. 7A, ROC plots 700, 702, 704, and 706 are generated by a clinical predictor performing a treatment response of an ovarian cancer patient based on a machine learning model similar to, for example, neural network 470 of FIG. 4C. For each ROC plot, feature vectors are input to the machine learning model to make a clinical prediction, with the prediction threshold generated based on a percentage of the input feature vectors. The true positive rates (TPR) against the false positive rates (TPR) of the machine learning model are obtained for different prediction thresholds based on varying the percentage of the input feature vectors, to obtain the ROC plots.

ROC plots 700, 702 and 704 plots are generated by inputting a single modality of clinical data to a machine learning model trained based on the labelled single modality of clinical data, whereas ROC plot 706 is generated by inputting multimodal clinical data to a machine learning model trained based on labelled multimodal clinical data. Specifically, ROC plot 700 is obtained by inputting only feature vectors representing RNA-seq data to a machine learning model trained based on labelled (resistance or sensitive) RNA-seq data. ROC plot 702 is obtained by inputting only feature vectors representing miRNA-seq data to a machine learning model trained based on labelled (resistance or sensitive) miRNA-seq data. Moreover, ROC plot 704 is obtained by inputting only feature vectors representing biopsy image data (e.g., primary tumor) to a number of machine learning models (e.g., random forest (RForest), XGBoost, multilayer perceptron (MLP), and support vector machine (Linear SVC)) trained based on labelled (resistance or sensitive) biopsy image data.

In this experiment, the biopsy image data comprise histopathology images including top and bottom frozen slides of primary tumor biopsies stained with H&E (hematoxylin and eosin) and is processed using machine learning model 450 of FIG. 4C to extract image features. Machine learning model 450 may include a CNN. As another example, a thresholding operation can be performed to convert the H&E biopsy images into binary images, and the binary image can be input to a machine learning model such as VGG-16 to extract the image features. The image features may represent pixel intensities. On the other hand, the molecular data, such as RNA-seq, miRNA-seq, protein expression, etc., can be downloaded from a national clinical database, such as National Cancer Institute (NCI) Genome Data Commons (GDC) portal. The molecular data can be post-processed, such as normalization, mapping to a set of numerical codes to facilitate processing by the machine learning model, etc. The data are divided into two sets, one set for training the machine learning model, and another set for inputting into the trained machine learning model to perform the prediction. False positive rates and true positive rates are plotted as the detection thresholds are varied.

The AUC of ROC plots 700, 702, and 704 ranges between 0.45-0.56. In comparison, ROC plot 706 is obtained by inputting multimodal clinical data including RNA-seq data, miRNA-seq data, biopsy image data, and protein expression, and the maximum AUC in ROC plot 706 is improved to 0.59.

B. Experimental Results of Predicting Survival Rates of Lung Cancer Patients for Different Treatments Based on Kaplan-Meier (K-M) Plots FIG. 7B and FIG. 7C illustrate example Kaplan-Meier (K-M) plots of lung cancer patients showing their survival rates with respect time in response to immunotherapy and chemotherapy treatments. The immunotherapy treatment may include anti-PDL1 atezolizumab to bevacizumab. Feature vectors of multimodal clinical data of a lung cancer patient, such as genomics data, which include gene expressions of T cell markers CD8A, TNF, CD4, EOMES, CTLA4, ICOS, CXCL10, and CD274, and lymphocytes biopsy image data, can be processed by a machine learning model, such as machine learning model 490 of FIG. 4F, to perform a prediction of which of the immunotherapy or chemotherapy treatments improves the patient's survival rate more. The prediction can be based on the hazard ratio, with a lower hazard ratio indicating a higher likelihood of one of the treatment can lead to better survival rate than the other treatment.

Referring to FIG. 7B, K-M plot 712 plots the survival rates of a group of lung cancer patients in response to immunotherapy and chemotherapy. Moreover, K-M plot 714 plots the survival rates of a subset of the lung cancer patients whose genomics feature vectors (e.g., gene expressions of T cell markers) fall within a certain range, whereas K-M plot 716 plots the survival rates of another subset of the lung cancer patients whose lymphocytes image data feature vectors (e.g., cell count, cell densities, etc.) fall within a certain range. In all these plots, the hazard ratio ranges between 0.45 to 0.59, which are relatively high and may indicate that both treatments have similar effect to the survival rate for the entire group of patients (K-M plot 712) as a whole, and/or for the subset of patients in plots 714 and 716.

Referring to FIG. 7C, biopsy image data and molecular data of the group of lung cancer patients can be collected. The biopsy image data can be processed by machine learning model 450 of FIG. 4C to compute image feature vectors, such as lymphocytic cell density. The molecular data of the group of lung cancer patients can include presence or absence of certain antibodies, such as PDL1 antibodies, gene expressions of T cell markers CD8A, TNF, CD4, EOMES, CTLA4, ICOS, CXCL10, and CD274, etc. The molecular data can be converted to numerical feature vectors. Correlation values between pairs of feature vectors among the lung cancer patients can be determined as described in FIG. 4E, and feature vectors that have the highest correlation are identified. In FIG. 4C and FIG. 7C, feature vectors representing lymphocytic cell density and feature vectors representing gene expressions of T cell markers CD8A, TNF, CD4, EOMES, CTLA4, ICOS, CXCL10, and CD274 were found to have the highest correlation among the group of lung cancer patients who were the subject of the experiment.

The feature vectors representing lymphocytic cell density and feature vectors representing gene expressions of T cell markers of the group of patients are then divided into quadrants based on their magnitudes, and cohorts of patients are identified based on their lymphocytic cell density feature vectors and T cell markers feature vectors. In this experiment, cohorts 482 and 484 of FIG. 4E and FIG. 4F are identified from the group of lung cancer patients, with K-M plot 724 representing a result of survival rate analysis of cohort 482 and K-M plot 726 representing a result of survival rate analysis of cohort 484.

As shown in FIG. 7C, cohort 482 has a hazard ratio of 0.18, which provides a strong indicator of immunotherapy leading to better survival rate (compared with chemotherapy) of a patient having lymphocytic H&E image features and gene expressions of T cell markers matching those of cohort 482. In contrast, cohort 484 has a hazard ratio of 0.69, which indicates that chemotherapy and immunotherapy probably do not make much difference to the survival rate for a patient having lymphocytic H&E image features and gene expressions of T cell markers matching those of cohort 484.

The increased difference in the hazard ratios between cohorts 482 and 484 shows that the techniques described in FIG. 4D-FIG. 4F, which includes identifying highly correlated input feature vectors, classifying cohorts of patients based on those input feature vectors, and performing a clinical prediction based on the survival rate analyses of the cohorts, can improve the stratification of patients' responses to the immunotherapy and chemotherapy treatments based on T cell markers and lymphocytic densities of these patients, which allow more accurate prediction of a patient's response based on the patient's T cell markers and lymphocytic density.

VII. Computer System

Figure 8:
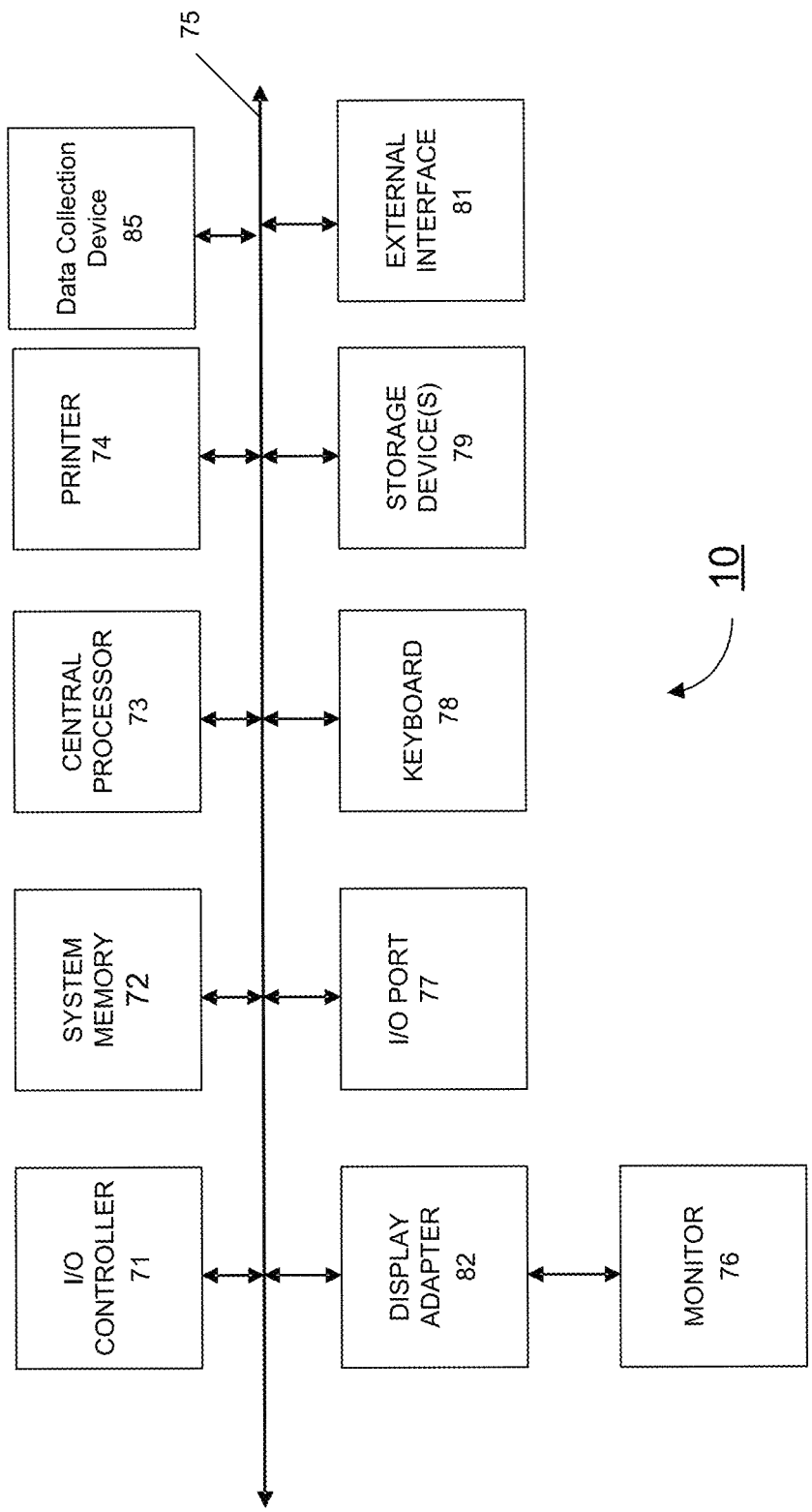
FIG. 8 illustrates an example computer system that may be utilized to implement techniques disclosed herein.

Any of the computer systems mentioned herein may utilize any suitable number of subsystems. Examples of such subsystems are shown in FIG. 8 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices. In some embodiments, a cloud infrastructure (e.g., Amazon Web Services), a graphical processing unit (GPU), etc., can be used to implement the disclosed techniques.

The subsystems shown in FIG. 8 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire®). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, units, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover reference to a "first" or a "second" component does not limit the referenced component to a particular location unless expressly stated.

All patents, patent applications, publications, and descriptions mentioned herein are incorporated by reference in their entirety for all purposes. None is admitted to be prior art.

What is claimed is:

1. A computer-implemented method of performing a clinical prediction, comprising:
   receiving first molecular data of a patient, the first molecular data including at least gene expressions of the patient;
   receiving first biopsy image data of the patient;
   processing, using a machine learning model comprising one or more of a random forest (RF) model, a support vector machine (SVM) model, or an artificial neural network model, the first molecular data and the first biopsy image data to perform a clinical prediction of the patient's response to a treatment, wherein the machine learning model is generated or updated based on second molecular data including at least gene expressions and second biopsy image data of a plurality of patients,
   wherein the machine learning model comprises:
      a first range of first feature vector magnitudes generated from the second molecular data comprising gene expressions of T cell markers;
      a second range of second feature vector magnitudes generated from the second biopsy image data comprising feature vectors of lymphocytic cells; and
      at least one of a survival rate or a hazard ratio generated from responses of a subset of the plurality of patients having first feature vector magnitudes falling within the first range and second feature vector magnitudes falling within the second range;
   wherein using the machine learning model includes:
      determining, based on the machine learning model, the at least one of the survival rate or the hazard ratio of the patient based on a third feature vector magnitude comprising gene expression of T cell markers generated from the first molecular data falling within the first range and a fourth feature vector magnitude generated from the first biopsy image data comprising a feature vector of lymphocytic cells falling within the second range, wherein the clinical prediction is based on the at least one of the survival rate or the hazard ratio; and
   generating an output of the clinical prediction.

2. The method of claim 1, wherein the clinical prediction comprises predicting whether the patient is resistant or sensitive to a platinum drug treatment for ovarian cancer.

3. The method of claim 2, wherein the patient is resistant to the platinum drug treatment for the ovarian cancer if the ovarian cancer recurs or progresses during a pre-determined period; and
   wherein the patient is sensitive to the platinum drug treatment for the ovarian cancer if no recurrence or progression of the ovarian cancer occurs during the pre-determined period.

4. The method of claim 3, wherein the output of the clinical prediction comprises a percentage value indicating a likelihood that the patient is sensitive to the platinum drug treatment for ovarian cancer; and
   wherein the method further comprises:
      comparing the percentage value against a threshold;
      responsive to determining that the percentage value exceeds the threshold, outputting an indication that the patient is likely to be sensitive to the platinum drug treatment to a health care provider to facilitate the health care provider administering the platinum drug treatment to the patient.

5. The method of claim 4, wherein the method further comprises:
   responsive to determining that the percentage value exceeds the threshold, administering the platinum drug treatment to the patient.

6. The method of claim 1, wherein the clinical prediction comprises predicting a first survival rate of the patient having a lung cancer in response to an immunotherapy treatment and a second survival rate of the patient in response to a chemotherapy treatment.

7. The method of claim 1, wherein the first and second molecular data comprise at least one of: one or more RNA-seq (ribonucleic acid (RNA)-sequencing) data, one or more microRNA-seq (miRNA sequencing) data, protein expression data, gene mutation data, deoxyribonucleic acid (DNA) methylation data, or copy number variation (CNV) data, or presence or absence of an antibody molecule in a patient.

8. The method of claim 1, wherein first and second biopsy image data comprise biopsy image data of a primary tumor.

9. The method of claim 8, wherein the first and second biopsy image data of primary tumor hematoxylin- and eosin-stained (H&E) histopathology data.

10. The method of claim 9, wherein the machine learning model is a first machine learning model; and
    wherein the first and second biopsy image data comprises feature data extracted from the H&E histopathology data using a second machine learning model.

11. The method of claim 10, wherein the second machine learning model comprises:
    a first stage model to generate first intermediate outputs representing identification of at least one of a shape or a boundary from pixel data of the first and second biopsy image data;
    a second stage model to perform a recognition operation on the first intermediate outputs to generate second intermediate outputs, the recognition operation comprising at least one of: a tissue segmentation operation to identify a tissue, a cell extraction operation to identify a cell, or a cell component extraction operation to identify a cell component; and a third stage model to compute feature data based on the second intermediate outputs, the feature data comprising at least one of: a tissue identified by the tissue segmentation operation, a count of a cell extracted by the cell extraction operation, a density of the cell extracted by the cell extraction operation.

12. The method of claim 11, wherein parameters of the second stage model and third stage model are trained based on labelled biopsy image data having annotation of the cell and the tissue.

13. The method of claim 12, wherein parameters of the first stage model are obtained from a transfer learning process.

14. The method of claim 1, wherein the machine learning model comprises a neural network model; and
wherein the neural network model is trained using the second molecular data and the second biopsy image data of the plurality of patients, the second molecular data and the second biopsy image data being labelled based on the responses of the plurality of patients to a treatment;
wherein the trained neural network model computes a score based on the first molecular data and the first biopsy image data; and
wherein the clinical prediction is based on the score.

15. The method of claim 14, wherein the treatment is a platinum drug treatment, and wherein the plurality of patients comprise: a first group of ovarian cancer patients who are sensitive to the platinum drug treatment, and a second group of ovarian cancer patients who are resistant to the platinum drug treatment;
wherein the second molecular data comprise sensitive-labelled molecular data associated with a sensitive label and obtained from at least some of the first group of ovarian cancer patients, and resistant-labelled molecular data associated with a resistant label and obtained from at least some of the second group of ovarian cancer patients; and
wherein the second biopsy image data comprise sensitive-labelled biopsy image data associated with the sensitive label and obtained from at least some of the first group of ovarian cancer patients, and resistant-labelled biopsy image data associated with the resistant label and obtained from at least some of the second group of ovarian cancer patients.

16. The method of claim 15, further comprising:
extracting, from the sensitive-labelled molecular data and the sensitive-labelled biopsy image data, a subset of sensitive-labelled molecular data and a subset of sensitive-labelled biopsy image data obtained from a common subset of the first group of ovarian cancer patients;
extracting, from the resistant-labelled molecular data and the resistant-labelled biopsy image data, a subset of resistant-labelled molecular data and a subset of resistant-labelled biopsy image data obtained from a common subset of the second group of ovarian cancer patients; and
training the machine learning model based on training data comprising the subset of sensitive-labelled molecular data, the subset of sensitive-labelled biopsy image data, the subset of resistant-labelled molecular data, and the subset of resistant-labelled biopsy image data.

17. A non-transitory computer readable medium storing instructions that, when executed by a hardware processor, causes the hardware processor to:
receive first molecular data of a patient, the first molecular data including at least gene expressions of the patient;
receive first biopsy image data of the patient;
process, using a machine learning model comprising one or more of a random forest (RF) model, a support vector machine (SVM) model, or an artificial neural network model, the first molecular data and the first biopsy image data to perform a clinical prediction of the patient's response to a treatment, wherein the machine learning model is generated or updated based on second molecular data including at least gene expressions and second biopsy image data of a plurality of patients,
wherein the machine learning model comprises:
a first range of first feature vector magnitudes generated from the second molecular data comprising gene expressions of T cell markers;
a second range of second feature vector magnitudes generated from the second biopsy image data comprising feature vectors of lymphocytic cells; and
at least one of a survival rate or a hazard ratio generated from responses of a subset of the plurality of patients having first feature vector magnitudes falling within the first range and second feature vector magnitudes falling within the second range;
wherein using the machine learning model includes:
determining, based on the machine learning model, the at least one of the survival rate or the hazard ratio of the patient based on a third feature vector magnitude comprising gene expression of T cell markers generated from the first molecular data falling within the first range and a fourth feature vector magnitude generated from the first biopsy image data comprising a feature vector of lymphocytic cells falling within the second range, wherein the clinical prediction is based on the at least one of the survival rate or the hazard ratio; and
generating an output of the clinical prediction.

18. The non-transitory computer readable medium of claim 17, wherein the clinical prediction comprises at least one of: predicting a risk of the patient having a disease, or predicting a survival rate of the patient in response to receiving the treatment.

19. A system comprising:
a memory that stores a set of instructions; and
a hardware processor configured to execute the set of instructions to:
receive first molecular data of a patient, the first molecular data including at least gene expressions of the patient;
receive first biopsy image data of the patient;
process, using a machine learning model comprising one or more of a random forest (RF) model, a support vector machine (SVM) model, or an artificial neural network model, the first molecular data and the first biopsy image data to perform a clinical prediction of the patient's response to a treatment, wherein the machine learning model is generated or updated based on second molecular data including at least gene expressions and second biopsy image data of a plurality of patients, wherein the machine learning model comprises:
  a first range of first feature vector magnitudes generated from the second molecular data comprising gene expressions of T cell markers;
  a second range of second feature vector magnitudes generated from the second biopsy image data comprising feature vectors of lymphocytic cells; and
  at least one of a survival rate or a hazard ratio generated from responses of a subset of the plurality of patients having first feature vector magnitudes falling within the first range and second feature vector magnitudes falling within the second range;
wherein using the machine learning model includes:
  determining, based on the machine learning model, the at least one of the survival rate or the hazard ratio of the patient based on a third feature vector magnitude comprising gene expression of T cell markers generated from the first molecular data falling within the first range and a fourth feature vector magnitude generated from the first biopsy image data comprising a feature vector of lymphocytic cells falling within the second range, wherein the clinical prediction is based on the at least one of the survival rate or the hazard ratio; and
generate an output of the clinical prediction.

* * * * *